(12) United States Patent
Quisenberry et al.

(10) Patent No.: US 10,512,587 B2
(45) Date of Patent: Dec. 24, 2019

(54) METHOD AND APPARATUS FOR SCALP THERMAL TREATMENT

(71) Applicant: ThermoTek, Inc., Flower Mound, TX (US)

(72) Inventors: Tony Quisenberry, Highland Village, TX (US); Niran Balachandran, Lewisville, TX (US); Sam K. McSpadden, Austin, TX (US)

(73) Assignee: ThermoTek, Inc., Flower Mound, TX (US)

( * ) Notice: Subject to any disclaimer, the term of this patent is extended or adjusted under 35 U.S.C. 154(b) by 0 days.

(21) Appl. No.: 15/784,379

(22) Filed: Oct. 16, 2017

(65) Prior Publication Data

US 2018/0055721 A1 Mar. 1, 2018

Related U.S. Application Data

(63) Continuation-in-part of application No. 13/558,615, filed on Jul. 26, 2012, now abandoned.
(Continued)

(51) Int. Cl.
*A61H 9/00* (2006.01)
*A61F 7/02* (2006.01)
*A61F 7/00* (2006.01)

(52) U.S. Cl.
CPC .......... *A61H 9/0092* (2013.01); *A61F 7/007* (2013.01); *A61F 7/02* (2013.01);
(Continued)

(58) Field of Classification Search
CPC ...... A61H 9/005; A61H 9/078; A61H 9/0092; A61H 2205/02–021; A61F 7/02;
(Continued)

(56) References Cited

U.S. PATENT DOCUMENTS

| 773,828 A | 11/1904 | Titus |
|---|---|---|
| 2,110,022 A | 3/1938 | Kliesrath |

(Continued)

FOREIGN PATENT DOCUMENTS

| CH | 670 541 | 6/1989 |
|---|---|---|
| DE | 35 22 127 | 1/1987 |

(Continued)

OTHER PUBLICATIONS

U.S. Appl. No. 12/730,060, Parish et al.
(Continued)

*Primary Examiner* — Rachel T Sippel
(74) *Attorney, Agent, or Firm* — Winstead PC

(57) ABSTRACT

A head wrap includes a body. A first arm extends from the body. A second arm extends from the body oppositely from, and shares a common axis with, the first arm. A center section extends from the body generally perpendicular to the first arm and the second arm. A first panel and a second panel extend from the first arm. A third panel and a fourth panel extending from the second arm. A fluid bladder is defined by the body, the first arm, the second arm, the center section, the first panel, the second panel, the third panel, and the fourth panel. A compression bladder is disposed outwardly of the fluid bladder and coextensive with the fluid bladder. A first fluid port is fluidly coupled to the fluid bladder and a second fluid port is fluidly coupled to the fluid bladder.

18 Claims, 21 Drawing Sheets

Related U.S. Application Data

(60) Provisional application No. 61/512,305, filed on Jul. 27, 2011.

(52) U.S. Cl.
CPC .............. *A61F 2007/0029* (2013.01); *A61F 2007/0039* (2013.01); *A61F 2007/0054* (2013.01); *A61F 2007/0071* (2013.01); *A61H 2201/0207* (2013.01); *A61H 2201/0228* (2013.01); *A61H 2205/06* (2013.01); *A61H 2205/10* (2013.01); *A61H 2205/106* (2013.01); *A61H 2205/12* (2013.01); *A61H 2209/00* (2013.01)

(58) Field of Classification Search
CPC ...... A61F 2007/0091; A61F 2007/0092; A61F 2007/0225–0233
See application file for complete search history.

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,179,106 A | 4/1965 | Meredith |
| 3,345,641 A | 10/1967 | Jennings |
| 3,367,319 A | 2/1968 | Carter, Jr. |
| 3,548,809 A | 12/1970 | Conti |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,419,988 A | 12/1983 | Mummert |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A | 6/1985 | Kuznetz |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,979,375 A | 10/1990 | Nathans et al. |
| 4,969,881 A | 11/1990 | Viesturs |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,261,399 A | 11/1993 | Klatz et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A | 5/1994 | Guibert et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,342,411 A | 8/1994 | Maxted et al. |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| 5,603,728 A | 2/1997 | Pachys |
| 5,636,643 A | 6/1997 | Argenta et al. |
| D380,874 S | 7/1997 | Caswell |

(56) References Cited

U.S. PATENT DOCUMENTS

| | | | |
|---|---|---|---|
| 5,645,081 | A | 7/1997 | Argenta et al. |
| 5,648,716 | A | 7/1997 | Devilbiss et al. |
| D383,546 | S | 9/1997 | Amis et al. |
| D383,547 | S | 9/1997 | Mason et al. |
| D383,848 | S | 9/1997 | Mason et al. |
| 5,662,695 | A | 9/1997 | Mason et al. |
| 5,669,872 | A | 9/1997 | Fox |
| 5,672,152 | A | 9/1997 | Mason et al. |
| 5,675,473 | A | 10/1997 | McDunn et al. |
| 5,682,748 | A | 11/1997 | DeVilbiss et al. |
| 5,689,957 | A | 11/1997 | DeVilbiss et al. |
| 5,690,849 | A | 11/1997 | DeVilbiss et al. |
| 5,711,029 | A | 1/1998 | Visco et al. |
| 5,711,155 | A | 1/1998 | DeVilbiss et al. |
| D393,073 | S | 3/1998 | Downing et al. |
| 5,731,954 | A | 3/1998 | Cheon |
| 5,733,321 | A | 3/1998 | Brink |
| D394,707 | S | 5/1998 | Tsubooka |
| 5,755,755 | A | 5/1998 | Panyard |
| 5,772,618 | A | 6/1998 | Mason et al. |
| 5,782,780 | A | 7/1998 | Mason et al. |
| 5,795,312 | A | 8/1998 | Dye |
| 5,807,294 | A | 9/1998 | Cawley et al. |
| 5,827,208 | A | 10/1998 | Mason |
| 5,831,824 | A | 11/1998 | McDunn et al. |
| D403,779 | S | 1/1999 | Davis et al. |
| D404,490 | S | 1/1999 | Tripolsky |
| D405,884 | S | 2/1999 | Roper |
| 5,865,841 | A | 2/1999 | Kolen et al. |
| 5,871,526 | A * | 2/1999 | Gibbs ................ A61F 7/02 165/46 |
| 5,890,371 | A | 4/1999 | Rajasubramanian et al. |
| 5,897,581 | A * | 4/1999 | Fronda ................ A61F 7/10 607/109 |
| 5,901,037 | A | 5/1999 | Hamilton et al. |
| 5,913,885 | A | 6/1999 | Klatz et al. |
| 5,923,533 | A | 7/1999 | Olson |
| 5,947,914 | A | 9/1999 | Augustine |
| 5,950,234 | A | 9/1999 | Leong et al. |
| 5,980,561 | A | 11/1999 | Kolen et al. |
| 5,989,285 | A | 11/1999 | DeVilbiss et al. |
| 6,007,559 | A | 12/1999 | Arkans |
| 6,030,412 | A | 2/2000 | Klatz et al. |
| 6,055,157 | A | 4/2000 | Bartilson |
| 6,058,010 | A | 5/2000 | Schmidt et al. |
| 6,058,712 | A | 5/2000 | Rajasubramanian et al. |
| 6,080,120 | A | 6/2000 | Sandman et al. |
| D428,153 | S | 7/2000 | Davis |
| D430,288 | S | 8/2000 | Mason et al. |
| D430,289 | S | 8/2000 | Mason et al. |
| 6,117,164 | A | 9/2000 | Gildersleeve et al. |
| 6,125,036 | A | 9/2000 | Kang et al. |
| 6,129,688 | A | 10/2000 | Arkans |
| 6,135,116 | A | 10/2000 | Vogel et al. |
| 6,156,059 | A | 12/2000 | Olofsson |
| 6,176,869 | B1 | 1/2001 | Mason et al. |
| 6,178,562 | B1 * | 1/2001 | Elkins ................ A41D 13/005 2/102 |
| 6,186,977 | B1 | 2/2001 | Andrews et al. |
| 6,231,532 | B1 | 5/2001 | Watson et al. |
| 6,235,049 | B1 | 5/2001 | Nazerian |
| 6,238,427 | B1 | 5/2001 | Matta |
| 6,260,890 | B1 | 7/2001 | Mason |
| 6,270,481 | B1 | 8/2001 | Mason et al. |
| 6,277,143 | B1 | 8/2001 | Klatz et al. |
| 6,295,819 | B1 | 10/2001 | Mathiprakasam et al. |
| 6,305,180 | B1 | 10/2001 | Miller et al. |
| 6,312,453 | B1 * | 11/2001 | Stefanile ................ A61F 7/10 607/108 |
| 6,319,114 | B1 | 11/2001 | Nair et al. |
| 6,352,550 | B1 | 3/2002 | Gildersleeve et al. |
| 6,358,219 | B1 | 3/2002 | Arkans |
| 6,368,592 | B1 | 4/2002 | Colton et al. |
| 6,436,064 | B1 | 8/2002 | Kloecker |
| 6,443,978 | B1 | 9/2002 | Zharov |
| 6,462,949 | B1 | 10/2002 | Parish, IV et al. |
| 6,463,336 | B1 | 10/2002 | Mawhinney |
| 6,468,237 | B1 | 10/2002 | Lina |
| 6,500,200 | B1 * | 12/2002 | Kushnir ................ A61F 7/02 165/46 |
| 6,508,831 | B1 | 1/2003 | Kushnir |
| D472,322 | S | 3/2003 | Hoglund et al. |
| D473,315 | S | 4/2003 | Miros et al. |
| D473,656 | S | 4/2003 | Miros et al. |
| D473,948 | S | 4/2003 | Elkins et al. |
| 6,551,264 | B1 | 4/2003 | Cawley et al. |
| 6,551,347 | B1 | 4/2003 | Elkins |
| D474,544 | S | 5/2003 | Hoglund et al. |
| 6,562,060 | B1 | 5/2003 | Momtaheni |
| 6,592,535 | B2 | 7/2003 | Ravikumar |
| 6,596,016 | B1 | 7/2003 | Vreman |
| 6,648,904 | B2 | 11/2003 | Altshuler et al. |
| D484,601 | S | 12/2003 | Griffiths et al. |
| D484,602 | S | 12/2003 | Griffiths et al. |
| 6,660,027 | B2 | 12/2003 | Gruszecki et al. |
| 6,667,883 | B1 | 12/2003 | Solis et al. |
| 6,675,072 | B1 | 1/2004 | Kerem |
| D486,870 | S | 2/2004 | Mason |
| 6,695,823 | B1 | 2/2004 | Lina et al. |
| 6,719,713 | B2 | 4/2004 | Mason |
| 6,719,728 | B2 | 4/2004 | Mason et al. |
| 6,736,787 | B1 | 5/2004 | McEwen et al. |
| D492,411 | S | 6/2004 | Bierman |
| 6,775,137 | B2 | 8/2004 | Chu et al. |
| D496,108 | S | 9/2004 | Machin et al. |
| 6,789,024 | B1 | 9/2004 | Kochan, Jr. et al. |
| 6,802,823 | B2 | 10/2004 | Mason |
| D499,846 | S | 12/2004 | Cesko |
| 6,834,712 | B2 | 12/2004 | Parish et al. |
| 6,846,295 | B1 | 1/2005 | Ben-Nun |
| 6,848,498 | B2 | 2/2005 | Seki et al. |
| 6,855,158 | B2 | 2/2005 | Stolpmann |
| 6,893,414 | B2 | 5/2005 | Goble et al. |
| D506,553 | S | 6/2005 | Tesluk |
| 6,935,409 | B1 | 8/2005 | Parish, IV et al. |
| 6,936,019 | B2 | 8/2005 | Mason |
| D510,140 | S | 9/2005 | Brown |
| 6,945,988 | B1 | 9/2005 | Jones |
| D510,626 | S | 10/2005 | Krahner et al. |
| 6,986,783 | B2 | 1/2006 | Gunn et al. |
| D515,218 | S | 2/2006 | McGuire et al. |
| 7,004,915 | B2 | 2/2006 | Boynton et al. |
| D523,147 | S | 6/2006 | Tesluk |
| 7,066,949 | B2 | 6/2006 | Gammons et al. |
| 7,081,128 | B2 | 7/2006 | Hart et al. |
| D533,668 | S | 12/2006 | Brown |
| 7,198,046 | B1 | 4/2007 | Argenta et al. |
| 7,216,651 | B2 | 5/2007 | Argenta et al. |
| D551,351 | S | 9/2007 | Silva |
| D551,352 | S | 9/2007 | Frangi |
| 7,306,568 | B2 | 12/2007 | Diana |
| 7,354,411 | B2 | 4/2008 | Perry et al. |
| D568,482 | S | 5/2008 | Gramza et al. |
| D569,985 | S | 5/2008 | Ganapathy et al. |
| 7,427,153 | B1 | 9/2008 | Jacobs et al. |
| 7,429,252 | B2 | 9/2008 | Sarangapani |
| 7,484,552 | B2 | 2/2009 | Pfahnl |
| 7,492,252 | B2 | 2/2009 | Maruyama |
| 7,524,286 | B2 | 4/2009 | Johnson |
| 7,532,953 | B2 | 5/2009 | Vogel |
| 7,553,306 | B1 | 6/2009 | Hunt et al. |
| D595,620 | S | 7/2009 | Kingsbury |
| D601,707 | S | 10/2009 | Chouiller |
| 7,608,066 | B2 | 10/2009 | Vogel |
| 7,618,382 | B2 | 11/2009 | Vogel et al. |
| D608,006 | S | 1/2010 | Avitable et al. |
| D612,947 | S | 3/2010 | Turtzo et al. |
| D613,870 | S | 4/2010 | Shust |
| 7,717,869 | B2 | 5/2010 | Eischen, Sr. |
| D618,358 | S | 6/2010 | Avitable et al. |
| D619,267 | S | 7/2010 | Beckwith et al. |
| D620,122 | S | 7/2010 | Cotton |
| 7,799,004 | B2 | 9/2010 | Tumey |
| 7,804,686 | B2 | 9/2010 | Parish et al. |

(56) References Cited

U.S. PATENT DOCUMENTS

| | | |
|---|---|---|
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| 7,811,269 B2 | 10/2010 | Boynton et al. |
| D627,896 S | 11/2010 | Matsuo et al. |
| D628,300 S | 11/2010 | Caden |
| 7,837,673 B2 | 11/2010 | Vogel |
| D630,759 S | 1/2011 | Matsuo et al. |
| 7,867,206 B2 | 1/2011 | Lockwood et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |
| 8,088,113 B2 | 1/2012 | Scherson et al. |
| 8,100,956 B2 | 1/2012 | Quisenberry et al. |
| 8,109,981 B2 | 2/2012 | Gertner et al. |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 | 4/2012 | Dolliver et al. |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 | 8/2012 | Miller |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 | 7/2014 | Eckstein et al. |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 | 9/2015 | Parish et al. |
| 9,132,057 B2 * | 9/2015 | Wilford ............... A61H 9/0092 |
| 9,180,041 B2 | 11/2015 | Parish et al. |
| 9,192,539 B2 | 11/2015 | Parish et al. |
| 9,669,233 B2 | 6/2017 | Quisenberry et al. |
| 2001/0018604 A1 | 8/2001 | Elkins |
| 2001/0039439 A1 | 11/2001 | Elkins et al. |
| 2002/0058976 A1 | 5/2002 | Lee |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0125649 A1 | 7/2003 | McIntosh et al. |
| 2003/0127215 A1 | 7/2003 | Parish, IV et al. |
| 2003/0135252 A1 | 7/2003 | MacHold et al. |
| 2003/0139255 A1 | 7/2003 | Lina |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1 | 9/2004 | Whelan et al. |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 | 6/2005 | Garrison et al. |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0035122 A1 | 2/2006 | Weissman et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0217787 A1 | 9/2006 | Olson et al. |
| 2006/0241549 A1 | 10/2006 | Sunnen |
| 2006/0253089 A1 | 11/2006 | Lin |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0239232 A1 | 10/2007 | Kurtz et al. |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103397 A1 | 5/2008 | Barak |
| 2008/0103422 A1 | 5/2008 | Perry et al. |
| 2008/0125775 A1 | 5/2008 | Morris |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |

(56) References Cited

U.S. PATENT DOCUMENTS

| | | | |
|---|---|---|---|
| 2008/0319362 A1 | 12/2008 | Joseph | |
| 2009/0069731 A1 | 3/2009 | Parish et al. | |
| 2009/0076475 A1 | 3/2009 | Ross et al. | |
| 2009/0109622 A1 | 4/2009 | Parish et al. | |
| 2009/0149821 A1 | 6/2009 | Scherson et al. | |
| 2009/0237264 A1 | 9/2009 | Bobey | |
| 2009/0254159 A1 | 10/2009 | Stormby | |
| 2009/0254160 A1 | 10/2009 | Shawver et al. | |
| 2010/0010477 A1 | 1/2010 | Augustine et al. | |
| 2010/0030306 A1 | 2/2010 | Edelman et al. | |
| 2010/0081975 A1 | 4/2010 | Avitable et al. | |
| 2010/0121230 A1 | 5/2010 | Vogel et al. | |
| 2010/0137764 A1 | 6/2010 | Eddy | |
| 2010/0145421 A1 | 6/2010 | Tomlinson et al. | |
| 2010/0150991 A1 | 6/2010 | Bernstein | |
| 2010/0160838 A1 | 6/2010 | Krespi | |
| 2010/0179469 A1 | 7/2010 | Hammond et al. | |
| 2010/0186436 A1* | 7/2010 | Stormby | A61F 7/10 |
| | | | 62/259.3 |
| 2010/0210982 A1 | 8/2010 | Balachandran et al. | |
| 2010/0249679 A1 | 9/2010 | Perry et al. | |
| 2010/0249680 A1 | 9/2010 | Davis | |
| 2011/0009785 A1 | 1/2011 | Meyer et al. | |
| 2011/0034861 A1 | 2/2011 | Schaefer | |
| 2011/0037002 A1 | 2/2011 | Johnson et al. | |
| 2011/0071447 A1 | 3/2011 | Liu et al. | |
| 2011/0082401 A1 | 4/2011 | Iker et al. | |
| 2011/0087142 A1 | 4/2011 | Ravikumar et al. | |
| 2011/0275983 A1 | 11/2011 | Quisenberry et al. | |
| 2011/0282269 A1 | 11/2011 | Quisenberry et al. | |
| 2012/0041526 A1 | 2/2012 | Stormby | |
| 2012/0130457 A1* | 5/2012 | Gammons | A61F 7/02 |
| | | | 607/104 |
| 2012/0259266 A1 | 10/2012 | Quisenberry | |
| 2012/0288848 A1* | 11/2012 | Latham | A61F 7/02 |
| | | | 435/1.1 |
| 2012/0289885 A1 | 11/2012 | Cottrell et al. | |
| 2013/0030331 A1 | 1/2013 | Quisenberry et al. | |
| 2013/0103123 A1 | 4/2013 | Khan et al. | |
| 2013/0116612 A1 | 5/2013 | Stephan | |
| 2013/0191437 A1 | 7/2013 | Itoh | |
| 2013/0216627 A1 | 8/2013 | Galbraith et al. | |
| 2013/0245508 A1 | 9/2013 | Maxon-Maldonado | |
| 2013/0245519 A1 | 9/2013 | Edelman et al. | |
| 2013/0253383 A1 | 9/2013 | Maxon-Maldonado | |
| 2013/0261512 A1 | 10/2013 | Maxon-Maldonado et al. | |
| 2013/0281947 A1 | 10/2013 | Quisenberry | |
| 2013/0331767 A1 | 12/2013 | Quisenberry | |
| 2014/0012169 A1 | 1/2014 | Wilford et al. | |
| 2014/0046410 A1 | 2/2014 | Wyatt | |
| 2014/0052054 A1 | 2/2014 | Quisenberry | |
| 2014/0236271 A1 | 8/2014 | Fronda et al. | |
| 2014/0257175 A1 | 9/2014 | Quisenberry | |
| 2014/0316330 A1 | 10/2014 | Fudem et al. | |
| 2014/0323949 A1 | 10/2014 | Quisenberry | |
| 2015/0133849 A1 | 5/2015 | Quisenberry et al. | |
| 2015/0290364 A1 | 10/2015 | Wall et al. | |
| 2015/0328042 A1 | 11/2015 | Parish et al. | |
| 2016/0030236 A1 | 2/2016 | Parish et al. | |
| 2016/0067104 A1 | 3/2016 | Sarangapani et al. | |
| 2016/0082238 A1 | 3/2016 | Wells et al. | |
| 2016/0317348 A1 | 11/2016 | Banker | |
| 2016/0367396 A1* | 12/2016 | Triggiano | A61F 7/10 |
| 2017/0095395 A1* | 4/2017 | Wennen | A41D 1/00 |
| 2017/0119940 A1 | 5/2017 | Quisenberry | |

FOREIGN PATENT DOCUMENTS

| | | |
|---|---|---|
| EP | 0076074 A1 | 4/1983 |
| EP | 0 489 326 | 6/1992 |
| EP | 0864309 A2 | 9/1998 |
| GB | 2373444 A | 9/2002 |
| JP | 2009504246 A | 2/2009 |
| SU | 689674 | 10/1979 |
| WO | WO-82/04184 A1 | 12/1982 |
| WO | WO-1989009583 A2 | 10/1989 |
| WO | WO-93/09727 | 5/1993 |
| WO | WO-93/12708 A2 | 7/1993 |
| WO | WO-1996005873 A1 | 2/1996 |
| WO | WO-9807397 A1 | 2/1998 |
| WO | WO-1998016176 A1 | 4/1998 |
| WO | WO-00/40186 | 7/2000 |
| WO | WO-01/14012 A1 | 3/2001 |
| WO | WO-01/54635 A1 | 8/2001 |
| WO | WO-03/047479 A1 | 6/2003 |
| WO | WO-2004105676 A1 | 12/2004 |
| WO | WO-2005046760 A1 | 5/2005 |
| WO | WO-2007019038 A2 | 2/2007 |
| WO | WO-2008099017 A1 | 8/2008 |
| WO | WO-2010124234 A1 | 10/2010 |
| WO | WO-2012067918 A1 | 5/2012 |

OTHER PUBLICATIONS

U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 13/796,139, Quisenberry.
U.S. Appl. No. 13/962,994, Quisenberry.
U.S. Appl. No. 14/062,428, Quisenberry.
U.S. Appl. No. 14/197,324, Quisenberry.
U.S. Appl. No. 15/227,417, filed Aug. 3, 2016, Overton et al.
U.S. Appl. No. 15/370,689, Quisenberry.
Artikis, T., PCT International Preliminary Report on Patentability as dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 as dated Apr. 2, 2008, 2 pages.
Young, Lee W., "International Search Report" for PCT/US07/08807 as dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210", filed Jan. 26, 2012.
Quisenberry, Tony, "U.S. Appl. No. 29/424,860", filed Jun. 15, 2012.
Quisenberry, Tony, "U.S. Appl. No. 13/456,410", filed Apr. 26, 2012.
Copenheaver, Blaine R., "International Search Report" for PCT/US2012/035096 as dated Aug. 7, 2012, 3 pages.
Quisenberry, Tony, "U.S. Appl. No. 13/558,615", filed Jul. 26, 2012.
Copenheaver, Blaine R., "International Search Report" prepared for PCT/US2013/030475 as dated May 23, 2013, 3 pages.
Young, Lee W., International Search Report of PCT Application No. PCT/US2014/64805, dated Mar. 13, 2015 (3 pages).
Hair Science Systems LLC, "Hair Science Systems—01 mobile unit—", Hair Saver Chemo Cold Cap, www.hairsciencesystems.com, 2 pages.
"U.S. FDA de novo clearance for the DigniCap® scalp cooling system that reduces hair loss related to chemotherapy for women

(56) References Cited

OTHER PUBLICATIONS with breast cancer", www.sysmex-europe.com/company/news-and-events/press-releases, accessed on Jun. 17, 2016, 3 pages.
"DigniLife—Prevention of Chermotherapy-Induced Alopecia", www.sysmex.co.uk/products/oncology/scalp-cooling-system-dignilife, accessed on Jun. 17, 2016, 3 pages.

\* cited by examiner

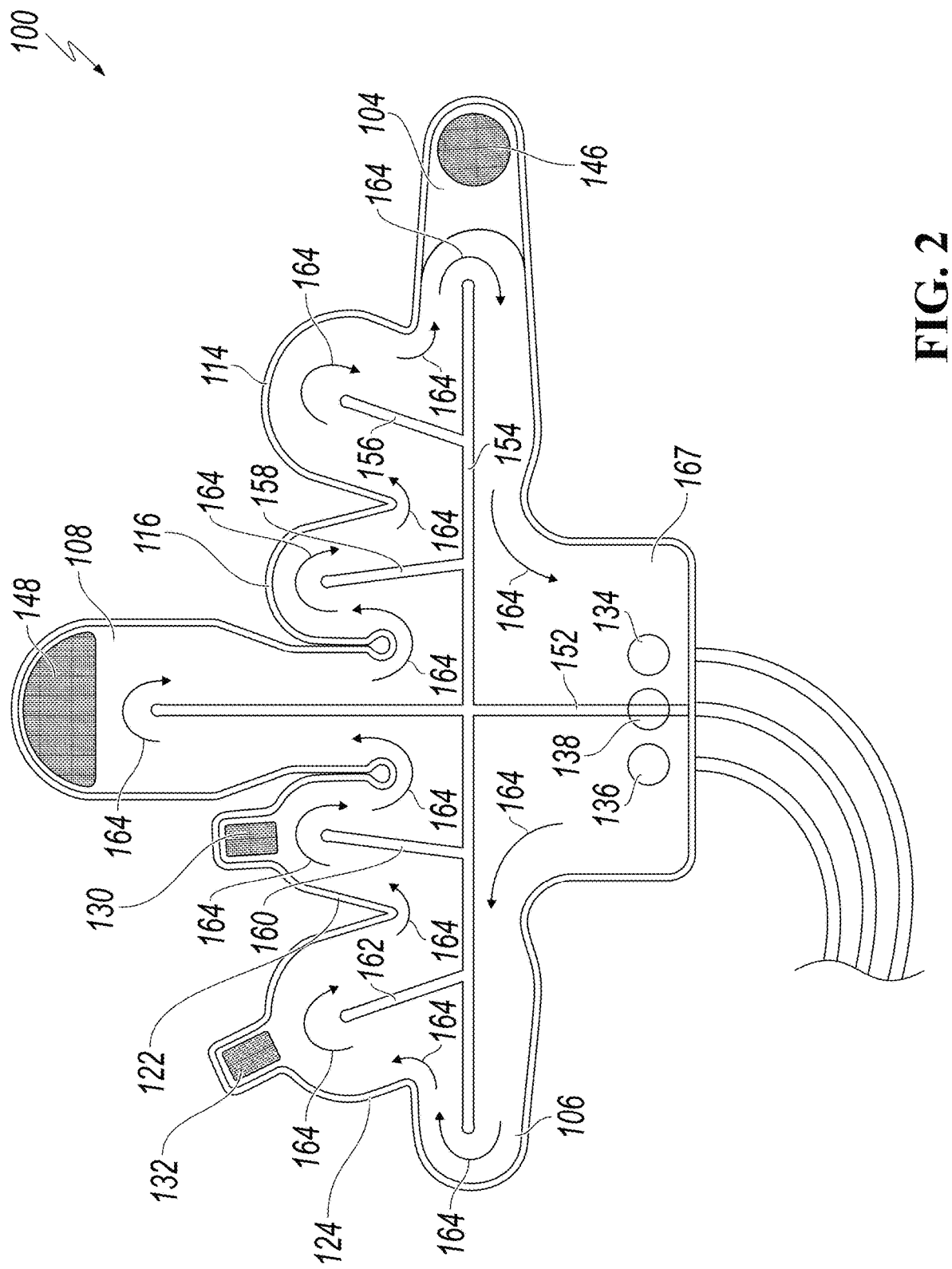

METHOD AND APPARATUS FOR SCALP THERMAL TREATMENT

CROSS-REFERENCE TO RELATED APPLICATIONS

This application is a continuation-in-part of U.S. patent application Ser. No. 13/558,615, filed on Jul. 26, 2012. U.S. patent application Ser. No. 13/558,615 claims priority to U.S. Provisional Patent Application No. 61/512,305, filed on Jul. 27, 2011. U.S. patent application Ser. No. 13/558,615 and U.S. Provisional Patent Application No. 61/512,305 are each incorporated herein by reference.

BACKGROUND

Field of the Invention

This disclosure relates generally to therapeutic head wraps and more specifically, but not by way of limitation to a therapeutic head wrap having a variety of adjustable panels to accommodate a variety of head shapes and utilizing compression to achieve better conformity and fitting against a head.

History of the Related Art

This section provides background information to facilitate a better understanding of the various aspects of the disclosure. It should be understood that the statements in this section of this document are to be read in this light, and not as admissions of prior art.

Treatments such as, for example, chemotherapy and radiation are widely used in the treatment of various types of cancer as well as other maladies. Such treatments often subject the body to one or more of harsh chemicals and radiation. In many cases, a side effect of such treatments includes the loss of bodily hair, a condition commonly known as "alopecia." Alopecia has been known, in many cases, to have a dramatic effect on a patient's comfort and self esteem. Consequently, efforts have been undertaken to ameliorate the alopecia-inducing effects of treatments including chemotherapy and radiation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one example, the disclosure relates to a head wrap that includes a body. A first arm extends from the body. A second arm extends from the body oppositely from, and shares a common horizontal axis with, the first arm. A center section extends from the body generally perpendicular to the first arm and the second arm. A first panel and a second panel extend from the first arm. A third panel and a fourth panel extending from the second arm. A fluid bladder is defined by the body, the first arm, the second arm, the center section, the first panel, the second panel, the third panel, and the fourth panel. A compression bladder is disposed outwardly of the fluid bladder and coextensive with the fluid bladder. A first fluid port is fluidly coupled to the fluid bladder and a second fluid port is fluidly coupled to the fluid bladder.

In another example, the disclosure relates to a method of using a head wrap includes applying a body to at least one of an occipital and a parietal region of a wearer's head. A first arm is coupled to a second arm. A first panel is coupled to a fourth panel. A second panel is coupled to a third panel. A center section is coupled to at least one of the first panel and the second panel. A compressed gas is applied to a compression bladder via a compression port. A heat-transfer fluid is circulated through a fluid bladder via a first fluid port and a second fluid port.

BRIEF DESCRIPTION OF THE DRAWINGS

The disclosure is best understood from the following detailed description when read with the accompanying drawings. It is emphasized that, in accordance with standard practice in the industry, various features are not drawn to scale. In fact, the dimensions of various features may be arbitrarily increased or reduced for clarity of discussion.

FIG. 2 is an interior plan view of the illustrative head wrap in the unfolded configuration;

DETAILED DESCRIPTION

Various embodiments of the present invention will now be described more fully with reference to the accompanying drawings. The invention may, however, be embodied in many different forms and should not be construed as limited to the embodiments set forth herein.

Figure 1A:
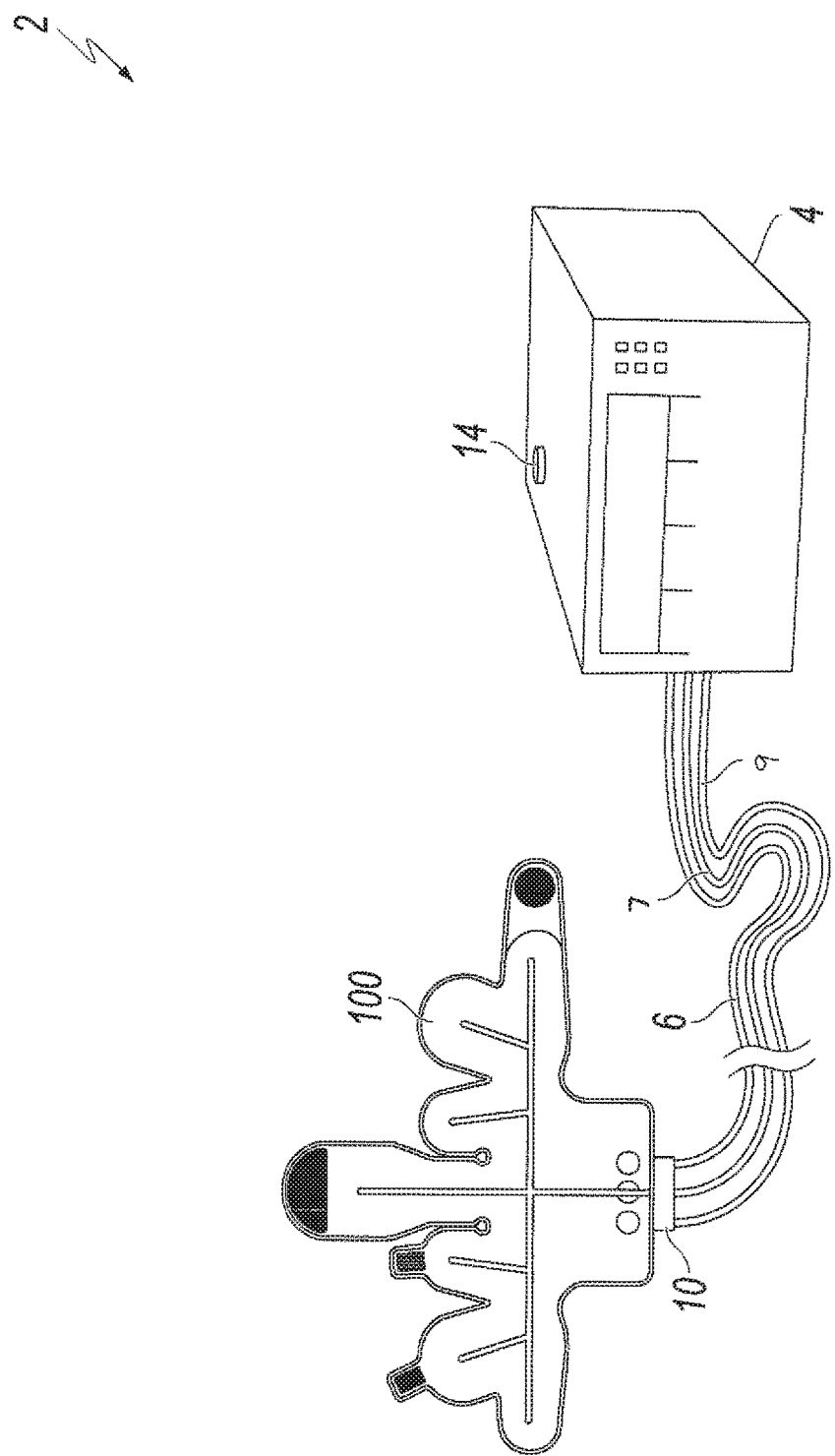
FIG. 1A is a schematic view of an illustrative therapy system.

Referring to FIG. 1A, there is shown a patient therapy system 2 according to the principles of the present disclosure. The patient therapy system 2 comprises a control unit 4, a head wrap 100, and a connector 10. In operation, a heat transfer fluid is deposited in the control unit 4 via an aperture 14. The heat transfer fluid is cooled or heated by the control unit 4 and pumped to the head wrap 100 by connector tube 6. The heat transfer fluid flows into the head wrap 100 through an inlet port, and exits through an outlet port to the control unit 4 via the connector 10 and connector tube 9. Similarly, a gas may be pumped by the control unit 4 to the head wrap 100 through the connector tube 7 and the connector 10 to provide compression. The connector tube 7 supplying gas is positioned between the connector tube 6 and the connector tube 9 supplying heat-transfer fluid. In this manner, the connector tube 7 supplying gas insulates the connector tube 6 from the connector tube 9. In addition, additional connector tubes may be present to allow for both heat transfer fluid and gas to be passed to the blanket for simultaneous temperature therapy and compression therapy.

The control unit 4 receives data and manipulates any one of a plurality of therapeutic characteristics of the head wrap 100 based on the data. The head wrap 100 is adapted for the administration of hot, cold, and/or compression therapies to a body portion of the patient. The connector 10 provides a fluid and/or gas connection between the control unit 4 and the head wrap 100 for the transfer of gas and heat transfer fluid. The connector 10 may also allow for transfer of electrical sensor signals and/or data signals between the head wrap 100 and the control unit 4.

Figure 1B:
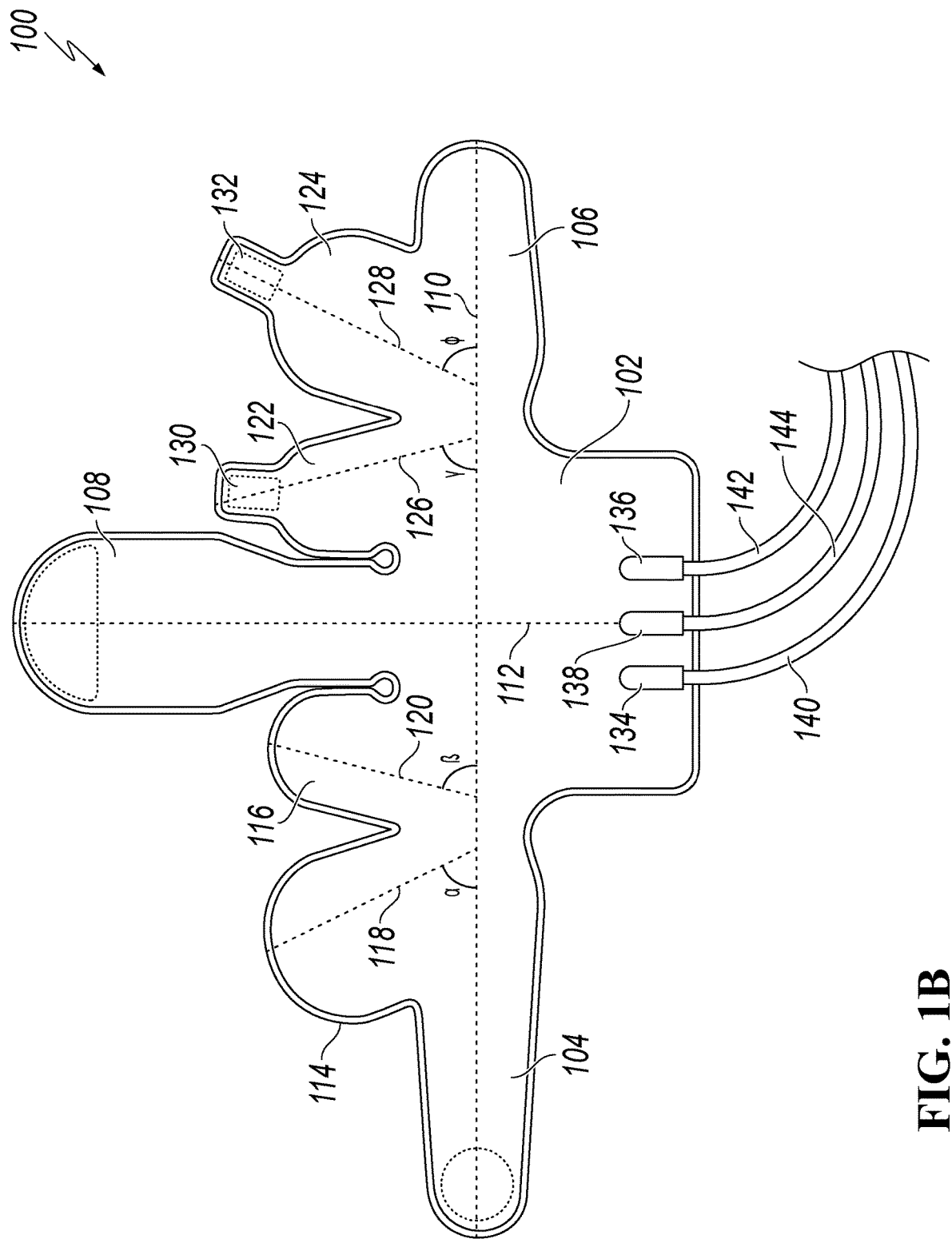
FIG. 1B is an exterior plan view of an illustrative head wrap in an unfolded configuration.

FIG. 1B is an exterior plan view of an illustrative head wrap 100 in an unfolded configuration in accordance with one or more aspects of the disclosure. The head wrap 100 includes a body 102. A first arm 104 and a second arm 106 extend laterally from the body 102 in generally opposite directions. The first arm 104 and the second arm 106 share a common central horizontal axis 110. A center section 108 extends from the body 102 such that a central vertical axis 112 of the center section 108 is generally perpendicular to the central horizontal axis 110 of the first arm 104 and the second arm 106. In various embodiments, however, the central vertical axis 112 of the center section 108 may be angled relative to the central horizontal axis 110 of the first arm 104 and the second arm 106. A first panel 114 and a second panel 116 extend from the first arm 104 on the same side as the center section 108. A first panel axis 118 is angled relative to the central horizontal axis 110 such that angle α is less than approximately 90 degrees. A second panel axis 120 is angled relative to the central horizontal axis 110 opposite the first panel axis 118 such that an angle β is less than approximately 90 degrees.

Still referring to FIG. 1B, a third panel 122 and a fourth panel 124 extend from the second arm 106 on the same side as the center section 108. A third panel axis 126 is angled relative to the central horizontal axis 110 such that an angle γ is less than approximately 90 degrees. A fourth panel axis 128 is angled relative to the central horizontal axis 110 opposite the third panel axis 126 such that an angle φ is less than approximately 90 degrees. The first panel axis 118 and the third panel axis 126 are arranged generally parallel to each other. Likewise, the second panel axis 120 and the fourth panel axis 128 are arranged generally parallel to each other. However, the first panel axis 118, the second panel axis 120, the third panel axis 126, and the fourth panel axis 128 could be arranged in any orientation. A first securement tab 130 extends from the third panel 122 and a second securement tab 132 extends from the fourth panel 124. In other embodiments, however, the first securement tab 130 could extend from the second panel 116 and the second securement tab 132 could extend from the first panel 114.

Still referring to FIG. 1B, a first fluid port 134 and a second fluid port 136 are disposed on the body 102 on opposite sides of the central vertical axis 112. A compression port 138 is disposed on the body 102 proximate the central vertical axis 112. The first fluid port 134 and the second fluid port 136 are fluidly coupled to a source of a heat-transfer fluid via a first tube 140 and a second tube 142, respectively. During operation, the first fluid port 134 facilitates delivery of the heat-transfer fluid to the head wrap 100 and the second fluid port 136 facilitates removal of the heat-transfer fluid from the head wrap 100. In various embodiments, however, the fluid flow is reversed such that the second fluid port 136 facilitates delivery of the heat-transfer fluid to the head wrap 100 and the first fluid port 134 facilitates removal of the heat-transfer fluid from the head wrap 100. The compression port 138 is fluidly coupled to a source of compressed gas via a third tube 144 and facilitates delivery of the compressed gas to the head wrap 100. The first tube 140, the second tube 142, and the third tube 144 are of sufficient length to allow the wearer to position the first tube 140, the second tube 142, and the third tube 144, for example, over the wearer's shoulder area and in front of the wearer. In other embodiments, the first tube 140, the second tube 142, and the third tube 144 are of sufficient length such as, for example, several feet, to connect to the control unit 4. The first tube 140 and the second tube 142 include a first coupler 143. The third tube 144 includes a second coupler 145. Use of the first coupler 143 and the second coupler 145 ensures that the first tube 140 and the second tube 142 cannot be connected to a, for example compressed gas source and, likewise, that the third tube 144 cannot be connected to, for example, a heat-transfer fluid source. The first coupler 143 and the second coupler 145 are, in a typical embodiment, keyed to the first tube 140, the second tube 142, and the third tube 144, respectively. Additionally, the first coupler 143 and the second coupler 145 are, during use, within reach of the wearer, thereby allowing the wearer to disconnect the head wrap 100 without assistance.

Figure 1C:
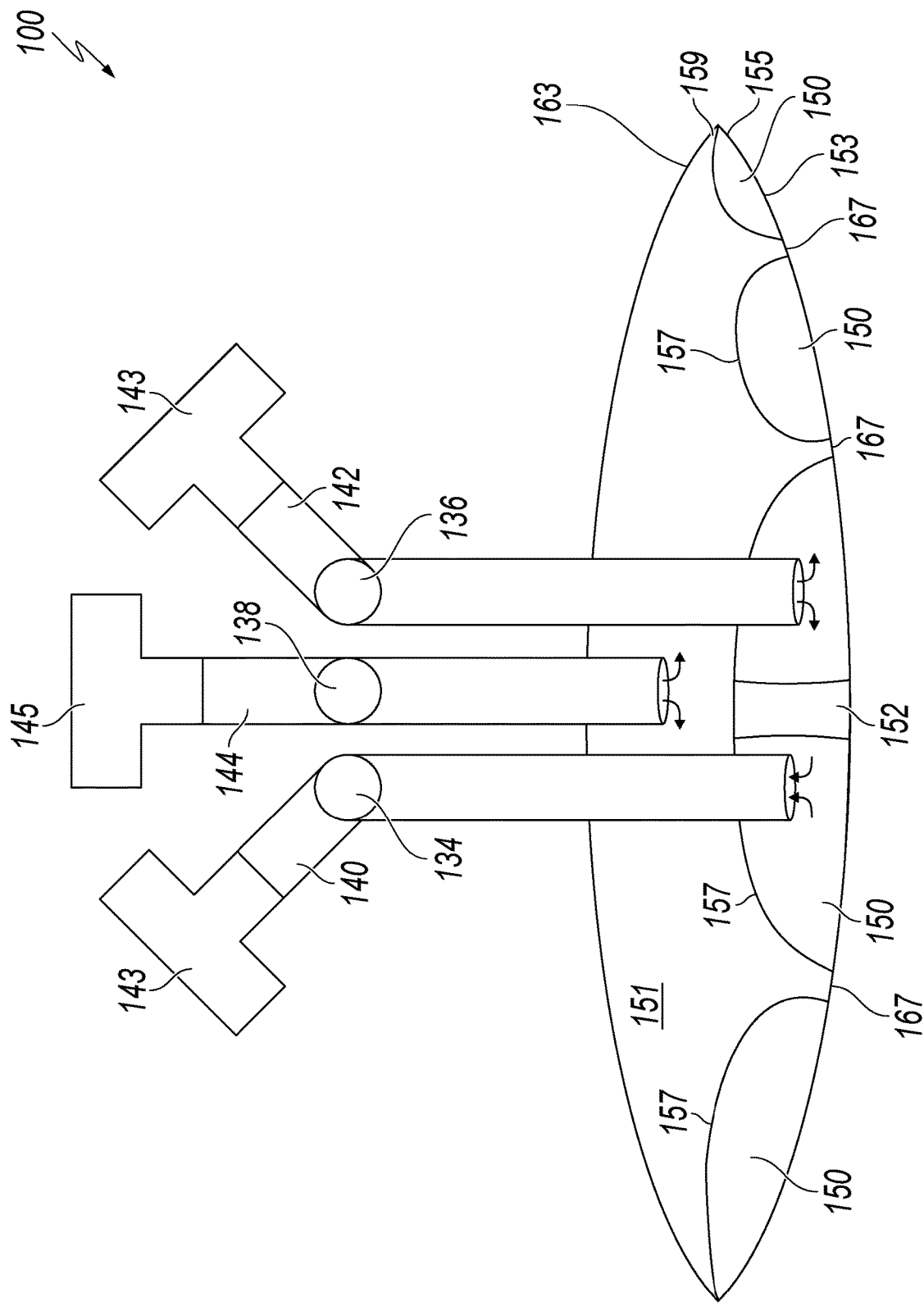
FIG. 1C is a cross sectional view of the illustrative head wrap.

FIG. 1C is a cross sectional view of the illustrative head wrap 100 in accordance with one or more aspects of the disclosure. The head wrap 100 includes a first layer 153 that is formed of a flexible material such as, for example, nylon, urethane, or polyvinyl chloride (PVC). The first layer 153 is adapted to be placed in contact with the wearer's scalp. The first layer 153 includes a first-layer perimeter 155. A second layer 157 is positioned adjacent to the first layer 153 and includes a second-layer perimeter 159 that aligns with and is bonded to the first-layer perimeter 155 such that a fluid bladder 150 is defined in the head wrap 100 between the first layer 153 and the second layer 157. A plurality of second bonds 167 are formed interior of the first-layer perimeter 155 and the second-layer perimeter 159. The plurality of second bonds 167 are, for example, circular in shape and join the first layer 153 to the second layer 157 at a plurality of intermediate points interior of the first-layer perimeter 155 and the second-layer perimeter 159. During operation, the plurality of second bonds 167 create a plurality of fluid flow paths through the fluid bladder 150. Additionally, the plurality of second bonds 167 limit an amount of heat-transfer fluid within the fluid bladder 150. Limiting the amount of heat-transfer fluid within the fluid bladder 150 reduces a weight of the head wrap 100 and improves comfort of the wearer. Furthermore, reducing an amount of heat-transfer fluid in the fluid bladder 150 prevents the head wrap 100 from assuming a rounded shape and losing contact with the wearer's scalp.

Still referring to FIG. 1C, in various embodiments, a third layer 161 is positioned adjacent to the second layer 157. The third layer 161 includes a third-layer perimeter 163 that aligns with and is bonded to the first-layer perimeter 155 and the second-layer perimeter 159 so as to define a compression bladder 151 between the second layer 157 and the third layer 161. The fluid bladder 150 is positioned on a scalp-facing side of the head wrap 100 such that, in use, a wearer's scalp is in contact with, and thermally exposed to, the fluid bladder 150. The first fluid port 134 and the second fluid port 136 are fluidly coupled to the fluid bladder. The first fluid port 134 facilitates delivery of a heat-transfer fluid to the fluid bladder 150 and the second fluid port 136 facilitates removal of the heat-transfer fluid from the fluid bladder 150. A first barrier 152 is formed in the fluid bladder 150 generally parallel to the central vertical axis 112. The first barrier 152 separates the first fluid port 134 from the second fluid port 136. A compression bladder 151 is formed in the head wrap 100. The compression bladder 151 is disposed outwardly of the fluid bladder 150 and fluidly coupled to the compression port 138. When a compressed gas is introduced to the compression bladder 151, a downward force is imparted on the fluid bladder 150. Such downward force ensures intimate contact of the fluid bladder 150 with the wearer's scalp and prevents puckering of the fluid bladder 150. Such puckering can cause areas of the wearer's scalp to not be sufficiently thermally exposed to the fluid bladder 150 resulting in small areas of alopecia on the wearer's scalp.

Figure 1D:
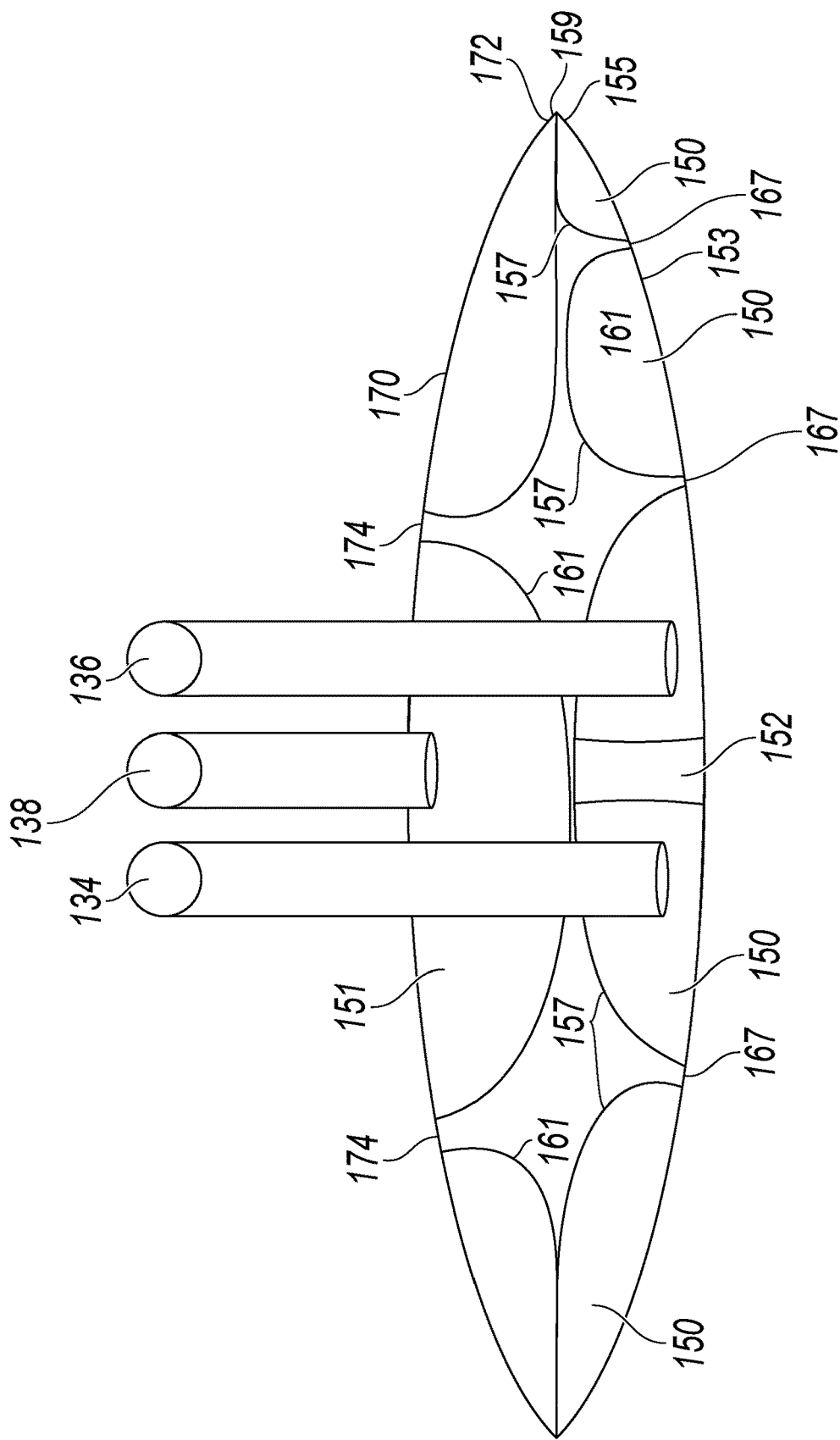
FIG. 1D is a cross sectional view of the illustrative head wrap showing a fourth layer.

FIG. 1D is a cross sectional view of the illustrative head wrap 100 showing a fourth layer 170 in accordance with one or more aspects of the disclosure. In various embodiments, the head wrap 100 includes a fourth layer 170 that is positioned outwardly of the third layer 161. The fourth layer 170 includes a fourth-layer perimeter 172 that is bonded to the third-layer perimeter 163 such that the compression bladder 151 is defined between the third layer 161 and the fourth layer 170. Additionally, third bonds 174 may be formed between the third layer 161 and the fourth layer 170 at select locations so as to selectively position compression across the wearer's scalp.

FIG. 2 is an interior plan view of the illustrative head wrap 100 in the unfolded configuration in accordance with one or more aspects of the disclosure. A third securement tab 146 is disposed on the first arm 104 and a fourth securement tab 148 is disposed on the center section 108. The fluid bladder 150 is formed on a scalp-facing side of the head wrap 100. The fluid bladder 150 is fluidly coupled to the first fluid port 134 and the second fluid port 136. A first barrier 152 is formed in the fluid bladder 150 generally parallel to the central vertical axis 112. The first barrier 152 separates the first fluid port 134 from the second fluid port 136. A second barrier 154 is formed in the fluid bladder 150 generally parallel to the central horizontal axis 110 and generally perpendicular to the first barrier 152. The second barrier 154 extends into, and directs flow of the heat-transfer fluid into, the first arm 104 and the second arm 106. A third barrier 156, a fourth barrier 158, a fifth barrier 160, and a sixth barrier 162 extend from the second barrier 154 into the first panel 114, the second panel 116, the third panel 122, and the fourth panel 124, respectively. In use, the third barrier 156, the fourth barrier 158, the fifth barrier 160, and the sixth barrier 162 direct the heat-transfer fluid into the first panel 114, the second panel 116, the third panel 122, respectively. During operation, the first barrier 152, the second barrier 154, the third barrier 156, the fourth barrier 158, the fifth barrier 160, and the sixth barrier 162 create a serpentine heat-transfer fluid flow path through the fluid bladder 150. The heat-transfer fluid flow path is illustrated by arrows 164; however, in other embodiments, the fluid flow could be in the direction opposite the arrows 164.

Figure 3:
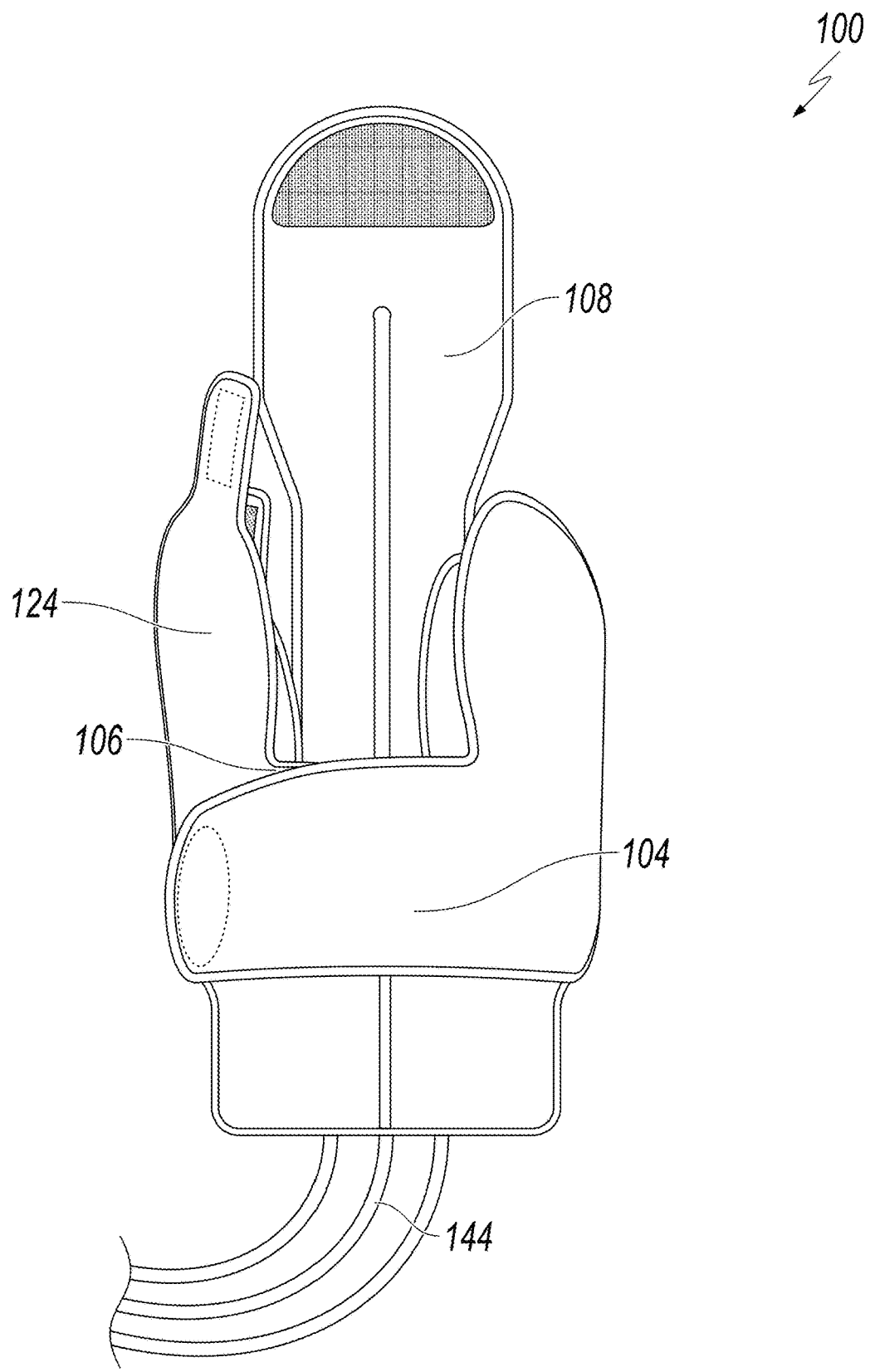
FIG. 3 is a front view of the illustrative head wrap in a partially-folded configuration wherein opposed arms have been coupled.

FIG. 3 is a front view of the illustrative head wrap 100 in a partially-folded configuration wherein the first arm 104 and the second arm 106 have been coupled to each other in accordance with one or more aspects of the disclosure. In use, the head wrap 100 is oriented such that an interior aspect of the body 102 is adjacent to an occipital region and a posterior neck region of a wearer. In this arrangement, the first tube 140, the second tube 142, and the third tube 144 extend down the wearer's back. The first arm 104 and the second arm 106 are wrapped around a circumference of the wearer's head. The first arm 104 overlaps the second arm 106 in the region of the wearer's forehead. The third securement tab 146 couples the first arm 104 to the second arm 106.

Figure 4A:
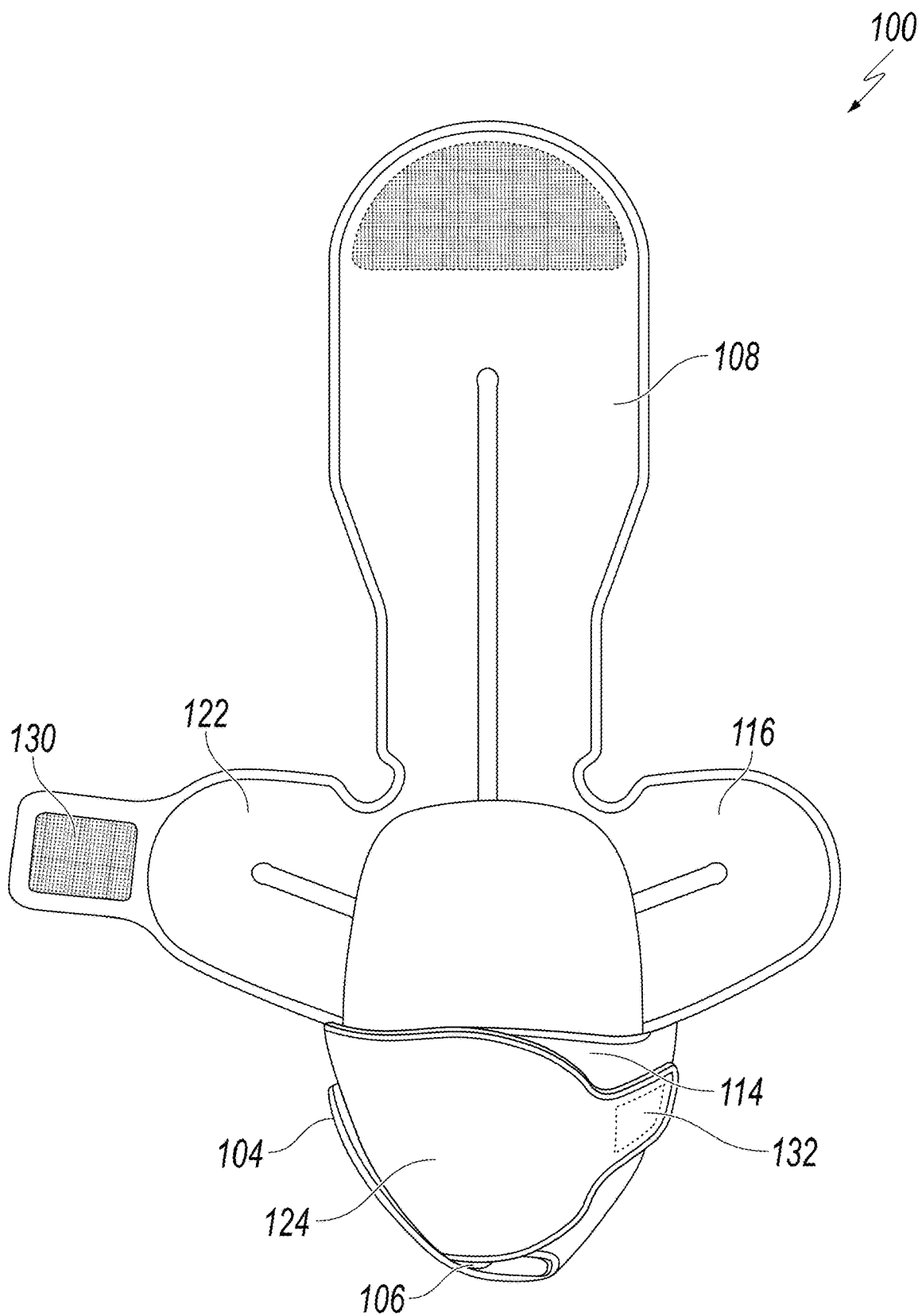
FIG. 4A is a top-front perspective view of the illustrative head wrap in a further partially-folded configuration wherein a first tab has been coupled to a second tab.

FIG. 4A is a top-front perspective view of the illustrative head wrap 100 in a further partially-folded configuration wherein the fourth panel 124 coupled to the first panel 114 in accordance with one or more aspects of the disclosure. In use, the first panel 114 and the fourth panel 124 are wrapped over an anterior top portion of the wearer's head. The fourth panel 124 at least partially overlaps the first panel 114. The second securement tab 132 couples the fourth panel 124 to the first panel 114.

Figure 4B:
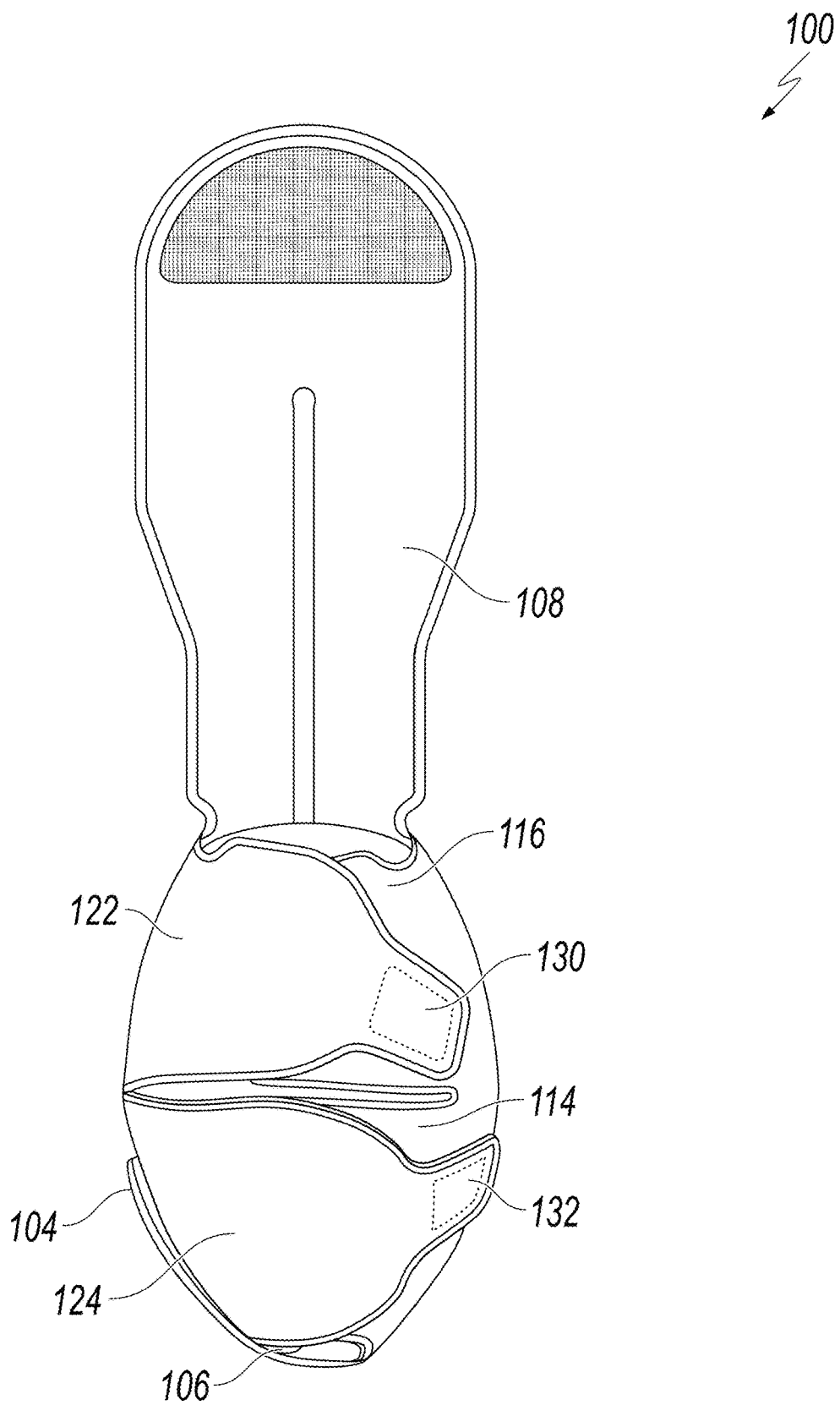
FIG. 4B is a top perspective view of the illustrative head wrap in a further partially-folded configuration wherein a third tab has been coupled to a fourth tab.

FIG. 4B is a top perspective view of the illustrative head wrap in a further partially-folded configuration wherein the third panel 122 has been coupled to the second panel 116 in accordance with one or more aspects of the disclosure. In use, the second panel 116 and the third panel 122 are wrapped over a posterior top portion of the wearer's head. The third panel 122 at least partially overlaps the second panel 116. The first securement tab 130 couples the third panel 122 to the second panel 116. Referring to FIGS. 4A and 4B collectively, the fourth panel 124 has been described by way of example as being coupled to the first panel 114. Likewise, the third panel 122 has been described by way of example as being coupled to the second panel 116. However, one skilled in the art will recognize that, in order to accommodate shapes of various wearer's heads, the third panel 122 may be coupled, via the first securement tab 130, to the first panel 114 and the fourth panel 124 may be coupled, via the second securement tab 132, to the second panel 116. In this manner, the first panel 114, the second panel 116, the third panel 122, and the fourth panel 124 may be coupled in any appropriate pattern to securely fit the head wrap 100 to the wearer's head.

Figure 5:
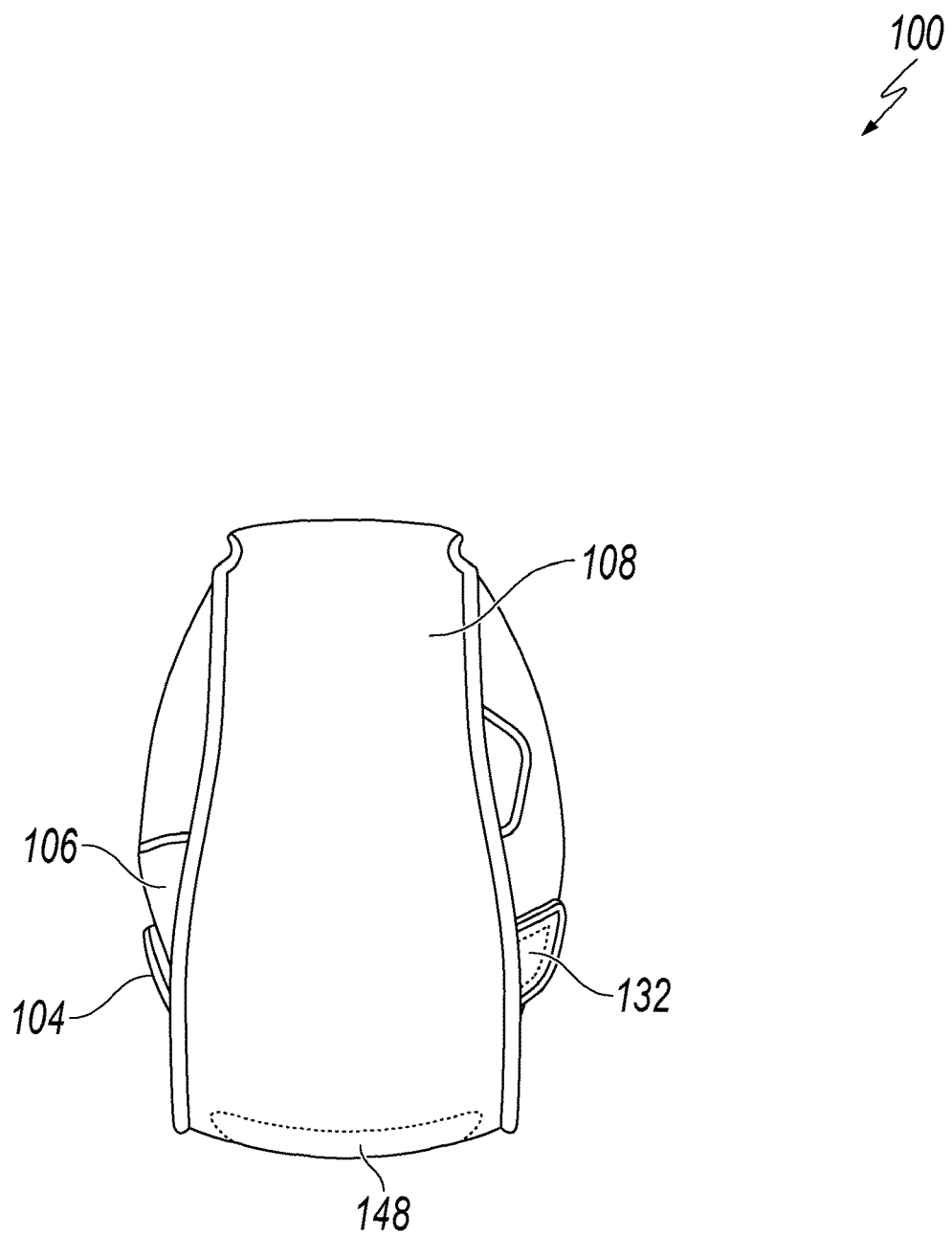
FIG. 5 is a top view of the illustrative head wrap in a fully-folded configuration wherein a center section has been folded.

FIG. 5 is a top view of the illustrative head wrap 100 in a fully-folded configuration wherein the center section 108 has been folded in accordance with one or more aspects of the disclosure. In use, the center section 108 is folded forward over a top of the wearer's head. The center section 108 at least partially overlaps the first panel 114, the second panel 116, the third panel 122, and the fourth panel 124. The center section 108 overlaps the first arm 104 and the second arm 106 in the region of the wearer's forehead. The fourth securement tab 148 couples the center section 108 to at least one of the first arm 104 and the second arm 106. As illustrated in FIGS. 2-5, the head wrap 100 is foldable from a generally flat configuration to a folded three-dimensional configuration to facilitate conformity and fitting against the wearer's scalp.

Figure 6A:
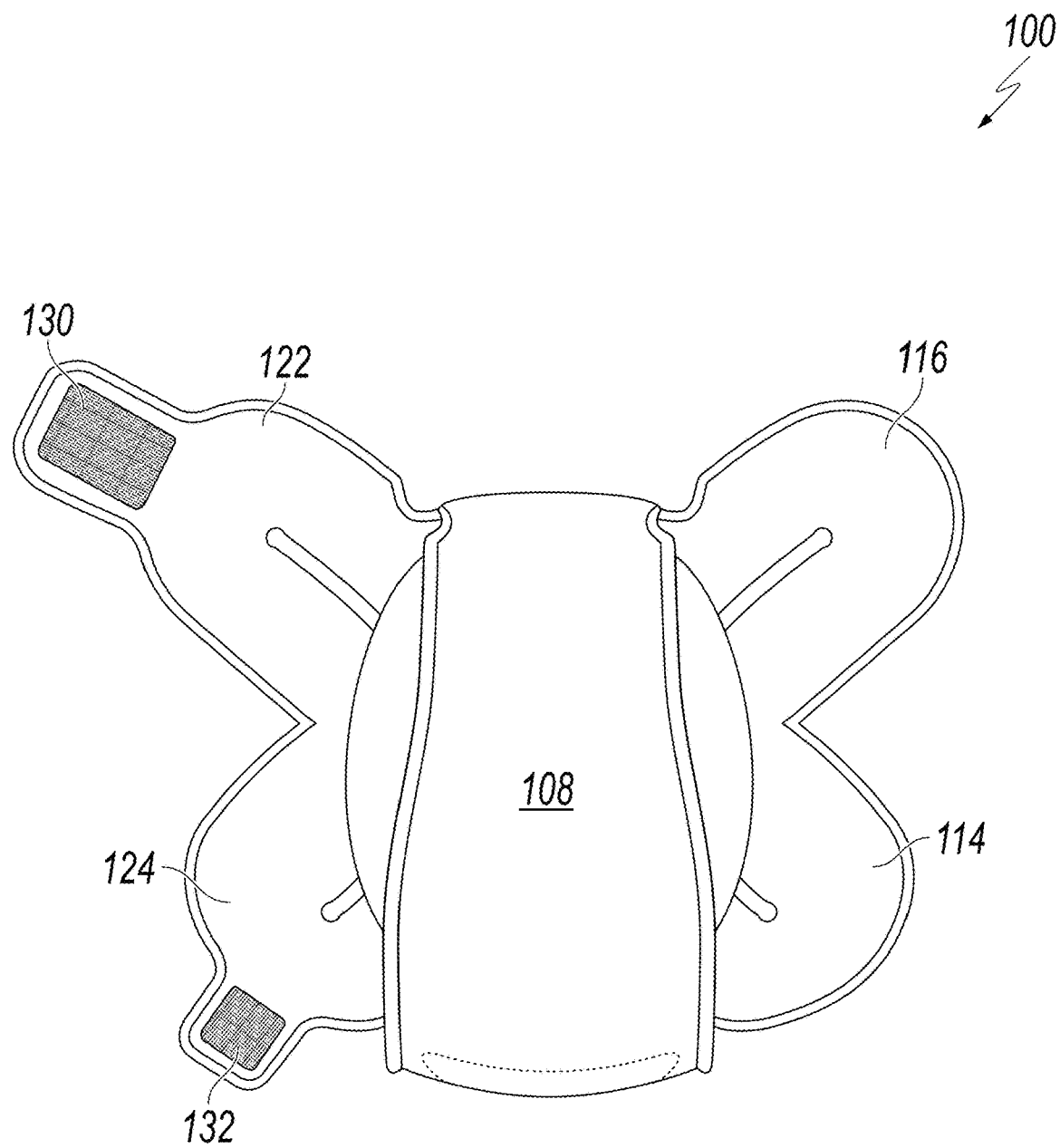
FIG. 6A is a top view of the illustrative head wrap in an alternate partially-folded configuration.
Figure 6B:
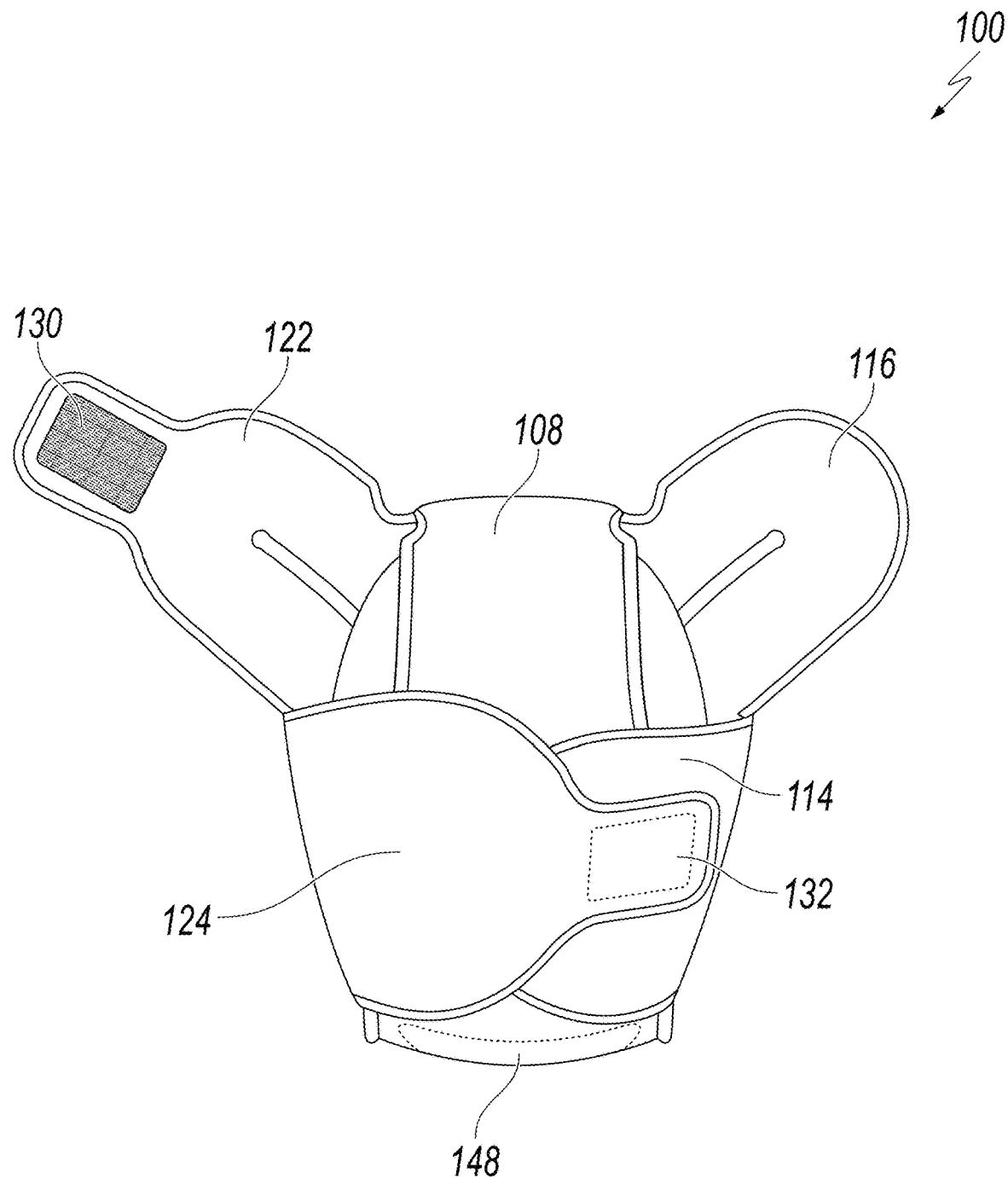
FIG. 6B is a top-front perspective view of the illustrative head wrap in a further partially-folded configuration wherein the fourth panel coupled to the first panel.
Figure 6C:
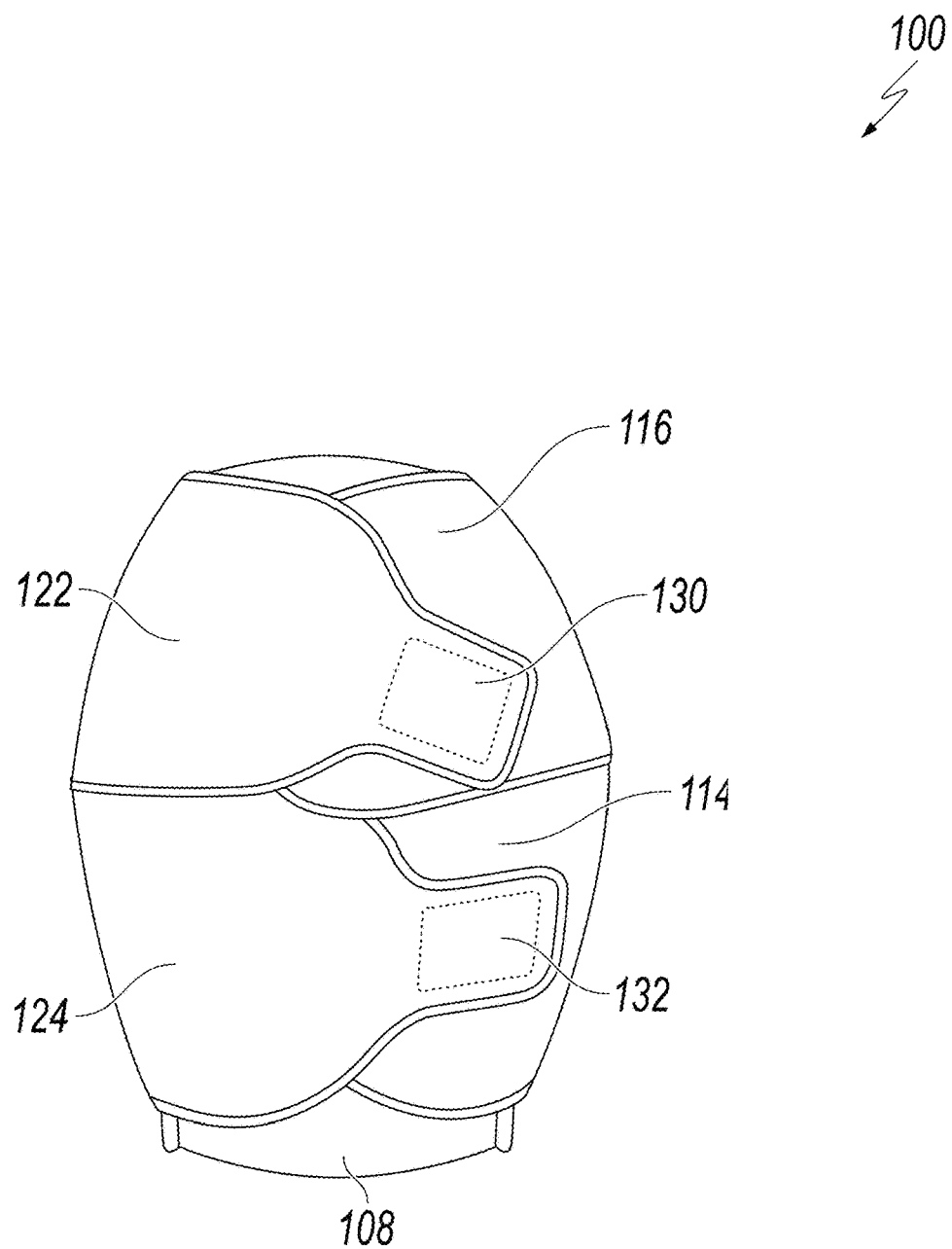
FIG. 6C is a top perspective view of the illustrative head wrap in a further partially-folded configuration wherein the third panel has been coupled to the second panel.

FIGS. 6A-6C are views of the illustrative head wrap 100 in various partially-folded configurations illustrating an alternative folding scheme of the head wrap 100. FIG. 6A is a top view of the illustrative head wrap 100 in a partially-folded configuration wherein the center section 108 has been folded in accordance with one or more aspects of the disclosure. In use, the center section 108 is folded forward over a top of the wearer's head. The center section 108 overlaps the first arm 104 and the second arm 106 in the region of the wearer's forehead. The fourth securement tab 148 couples the center section 108 to at least one of the first arm 104 and the second arm 106.

FIG. 6B is a top-front perspective view of the illustrative head wrap 100 in a further partially-folded configuration wherein the fourth panel 124 coupled to the first panel 114 in accordance with one or more aspects of the disclosure. In use, the first panel 114 and the fourth panel 124 are wrapped over an frontal portion of the wearer's head and over the folded center section 108. The fourth panel 124 at least partially overlaps the first panel 114. The second securement tab 132 couples the fourth panel 124 to the first panel 114.

FIG. 6C is a top perspective view of the illustrative head wrap in a further partially-folded configuration wherein the third panel 122 has been coupled to the second panel 116 in accordance with one or more aspects of the disclosure. In use, the second panel 116 and the third panel 122 are wrapped over a parietal portion of the wearer's head and over the folded center section 108. The third panel 122 at least partially overlaps the second panel 116. The first securement tab 130 couples the third panel 122 to the second panel 116. Referring to FIGS. 6B-6C collectively, the fourth panel 124 has been described by way of example as being coupled to the first panel 114. Likewise, the third panel 122 has been described by way of example as being coupled to the second panel 116. However, one skilled in the art will recognize that, in order to accommodate various shapes of different wearer's heads, the third panel 122 may be coupled, via the first securement tab 130, to the first panel 114 and the fourth panel 124 may be coupled, via the second securement tab 132, to the second panel 116. In this manner, the first panel 114, the second panel 116, the third panel 122, and the fourth panel 124 may be coupled in any appropriate pattern to securely fit the head wrap 100 in the desired position conforming to the wearer's head. As illustrated in FIGS. 6A-6C, the head wrap 100 is foldable from a generally flat configuration to a folded three-dimensional configuration to facilitate conformity and fitting against the wearer's scalp.

Figure 7A:
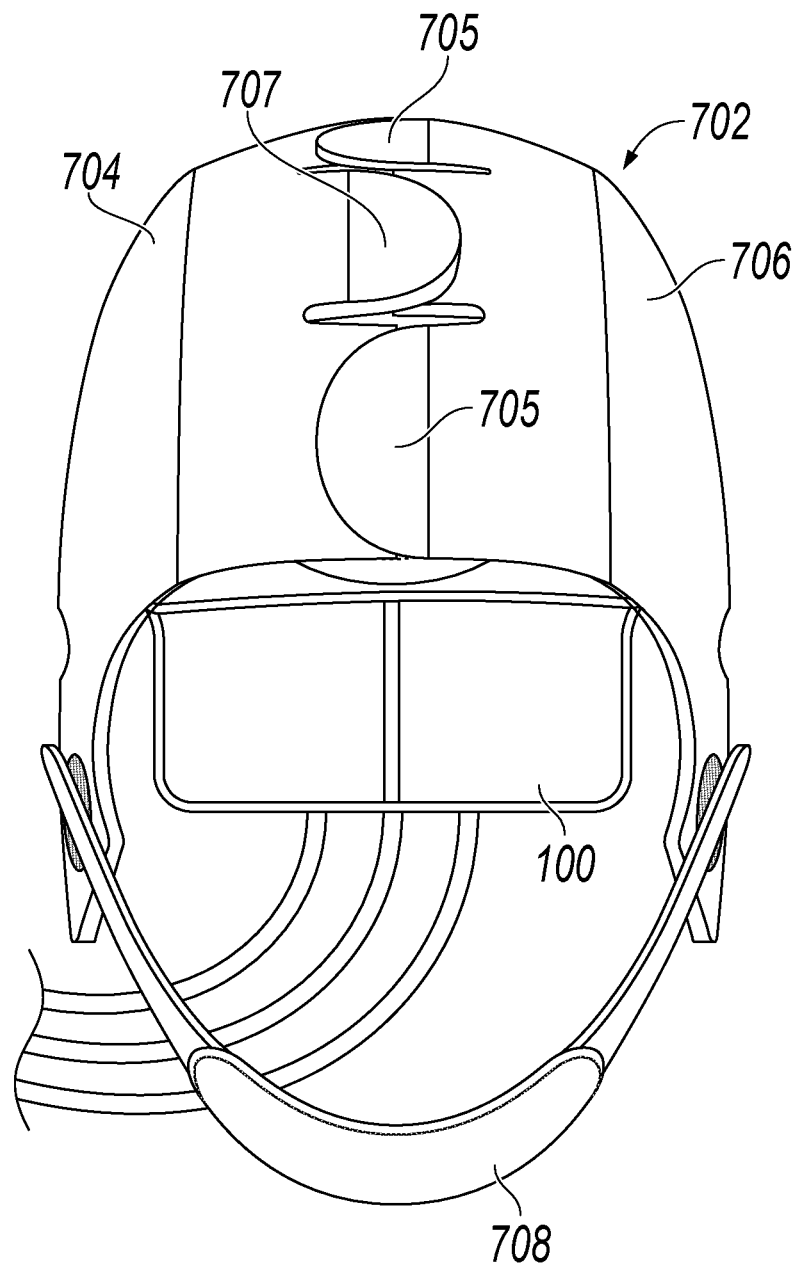
FIG. 7A is a front view of the illustrative head wrap in a fully-folded configuration showing a cap.
Figure 7B:
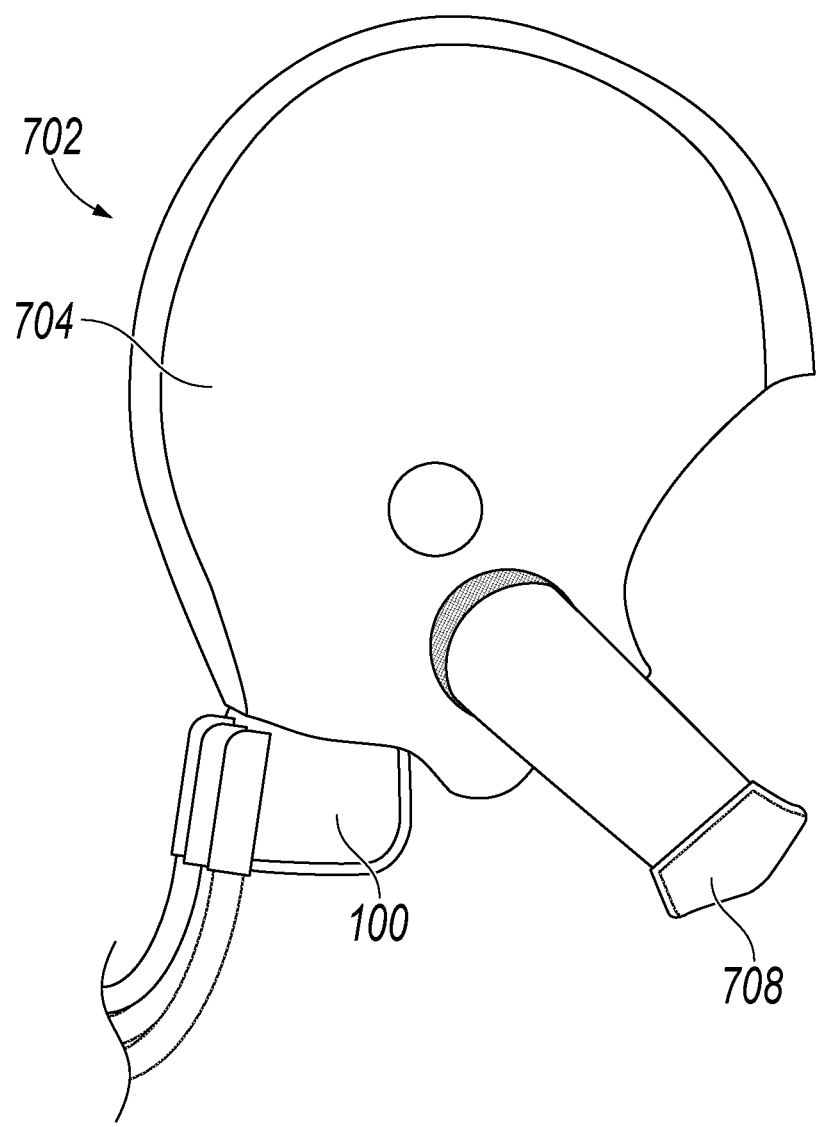
FIG. 7B is a side view of the illustrative head wrap in a fully-folded configuration showing a cap.
Figure 7C:
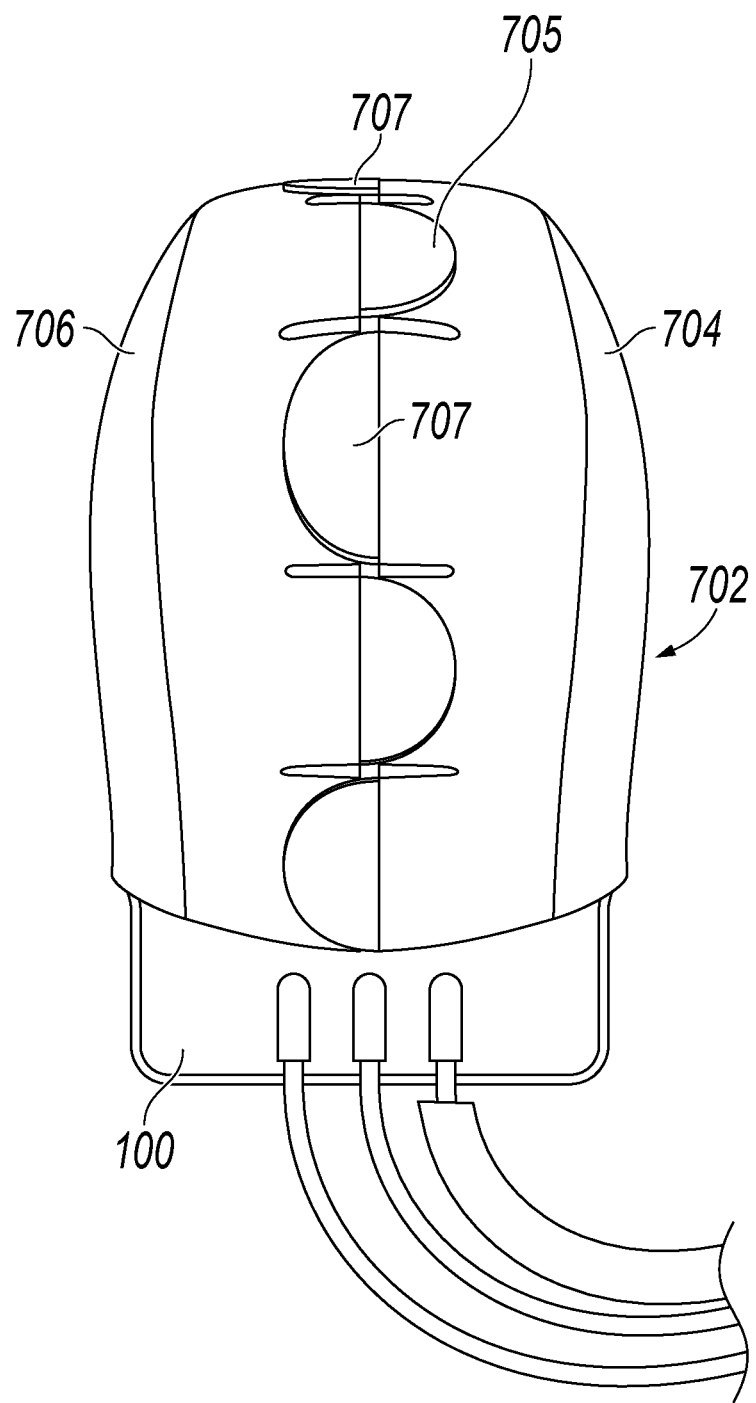
FIG. 7C is a rear view of the illustrative head wrap in a fully-folded configuration showing a cap.
Figure 7D:
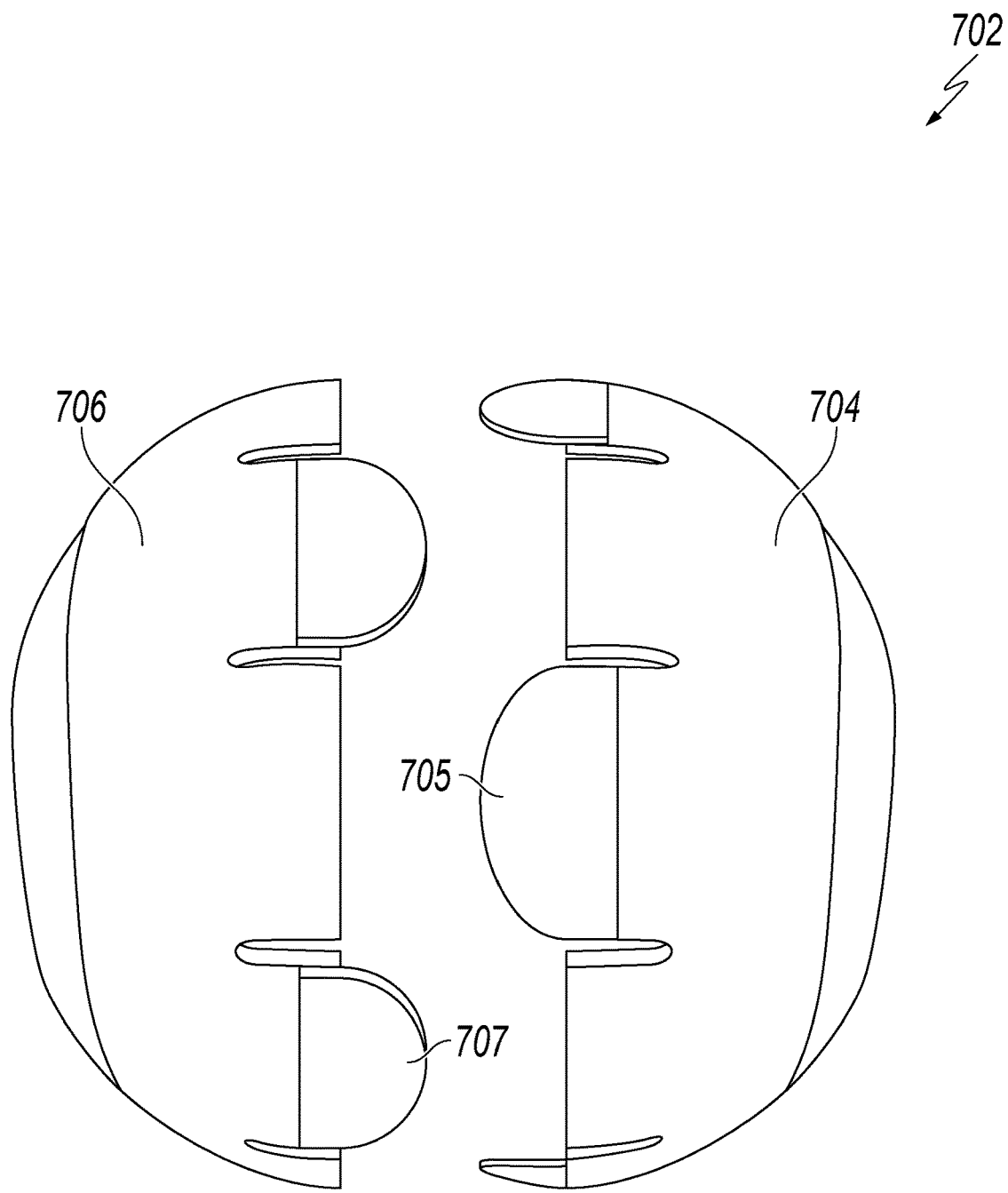
FIG. 7D is a top view of the illustrative head wrap in a fully-folded configuration showing a cap with a plurality of tabs de-coupled.
Figure 7E:
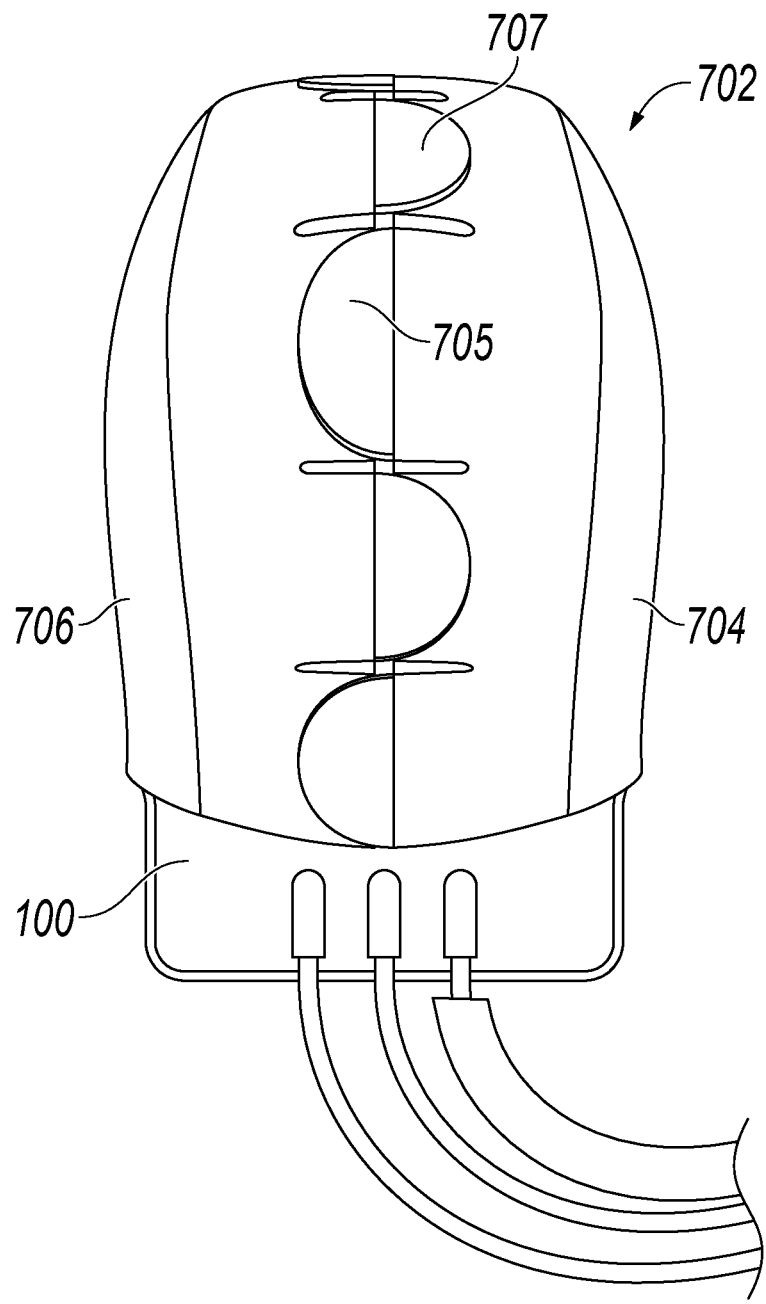
FIG. 7E is a top view of the illustrative head wrap in a fully-folded configuration showing a cap with a plurality of tabs coupled.

FIG. 7A is a front view of the illustrative head wrap 100 in a fully-folded configuration showing a cap 702 in accordance with one or more aspects of the disclosure. FIG. 7B is a side view of the illustrative head wrap 100 in a fully-folded configuration showing a cap 702 in accordance with one or more aspects of the disclosure. FIG. 7C is a rear view of the illustrative head wrap 100 in a fully-folded configuration showing a cap 702 in accordance with one or more aspects of the disclosure. FIG. 7D is a top view of the illustrative head wrap 100 in a fully-folded configuration showing a cap 702 with a plurality of tabs de-coupled in accordance with one or more aspects of the disclosure. FIG. 7E is a top view of the illustrative head wrap 100 in a fully-folded configuration showing a cap 702 with a plurality of tabs coupled in accordance with one or more aspects of the disclosure. A cap 702 is applied over the head wrap 100 and further secures the head wrap 100 to the wearer's head. The cap 702 includes a first half 704 having a first plurality of tabs 705 and a second half 706 having a second plurality of tabs 707. The first plurality of tabs 705 are selectively coupled to the second plurality of tabs 707 along a sagittal line so as to couple the first half 704 to the second half 706. In use, the first plurality of tabs 705 may be selectively coupled or de-coupled as desirable and necessary to the second plurality of tabs 707 in order to accommodate a variety of head shapes and achieve better conformity and fitting against a head. In use, a chin portion 708 extends under the wearer's chin in order to secure the cap 702 to the wearer's head. In various embodiments, the chin portion 708 extends over a temple region of the first half 704 and the second half 706 and is coupled to a crown region of the first half 704 and the second half 706. Thus, when the chin portion 708 is applied to the wearer's head, a force is transmitted through the chin portion 708 to the crown region of the first half 704 and the second half 706. Such an arrangement provides a downward force to the cap 702 and facilitates accommodation of a variety of head shapes and achieve better conformity and fitting against a head of a wearer.

Figure 8A:
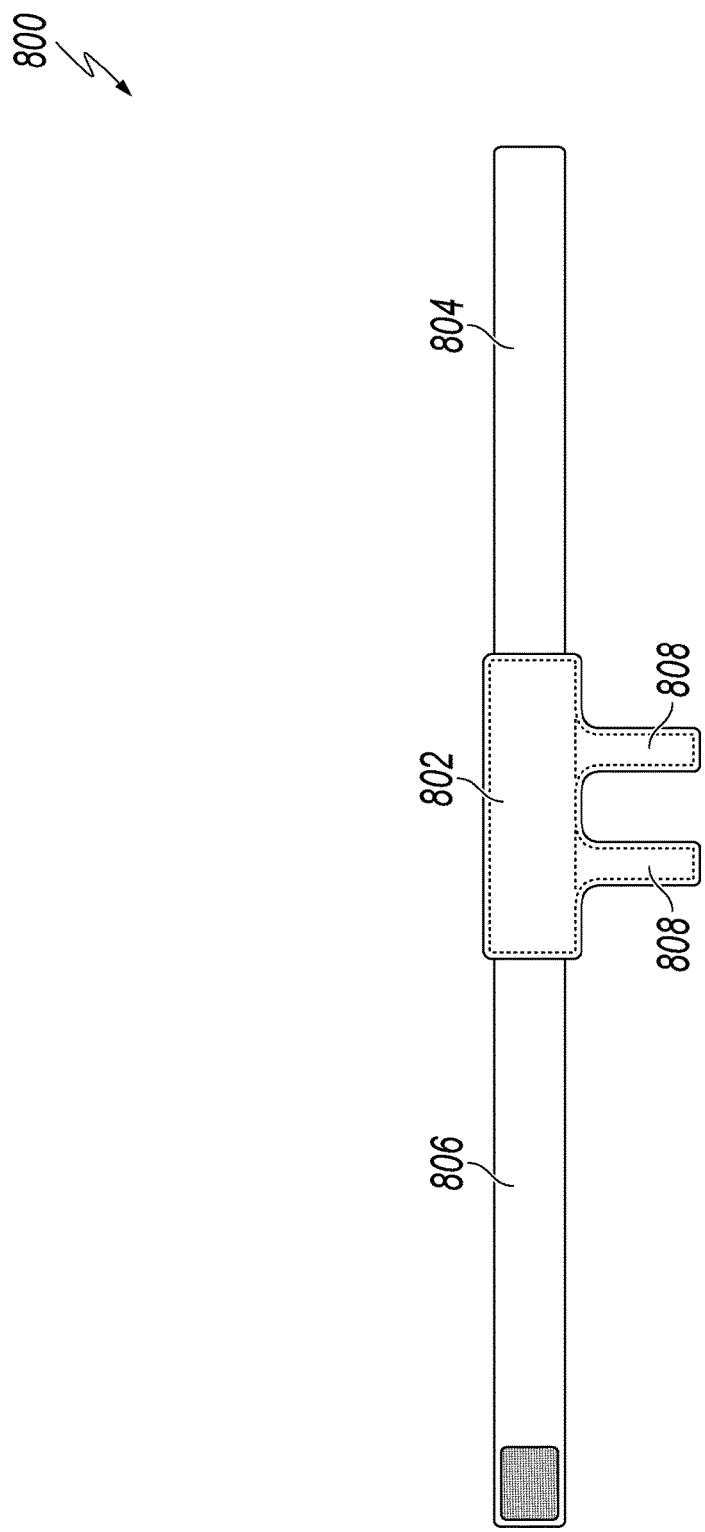
FIG. 8A is a perspective view of an illustrative cap securement device.
Figure 8B:
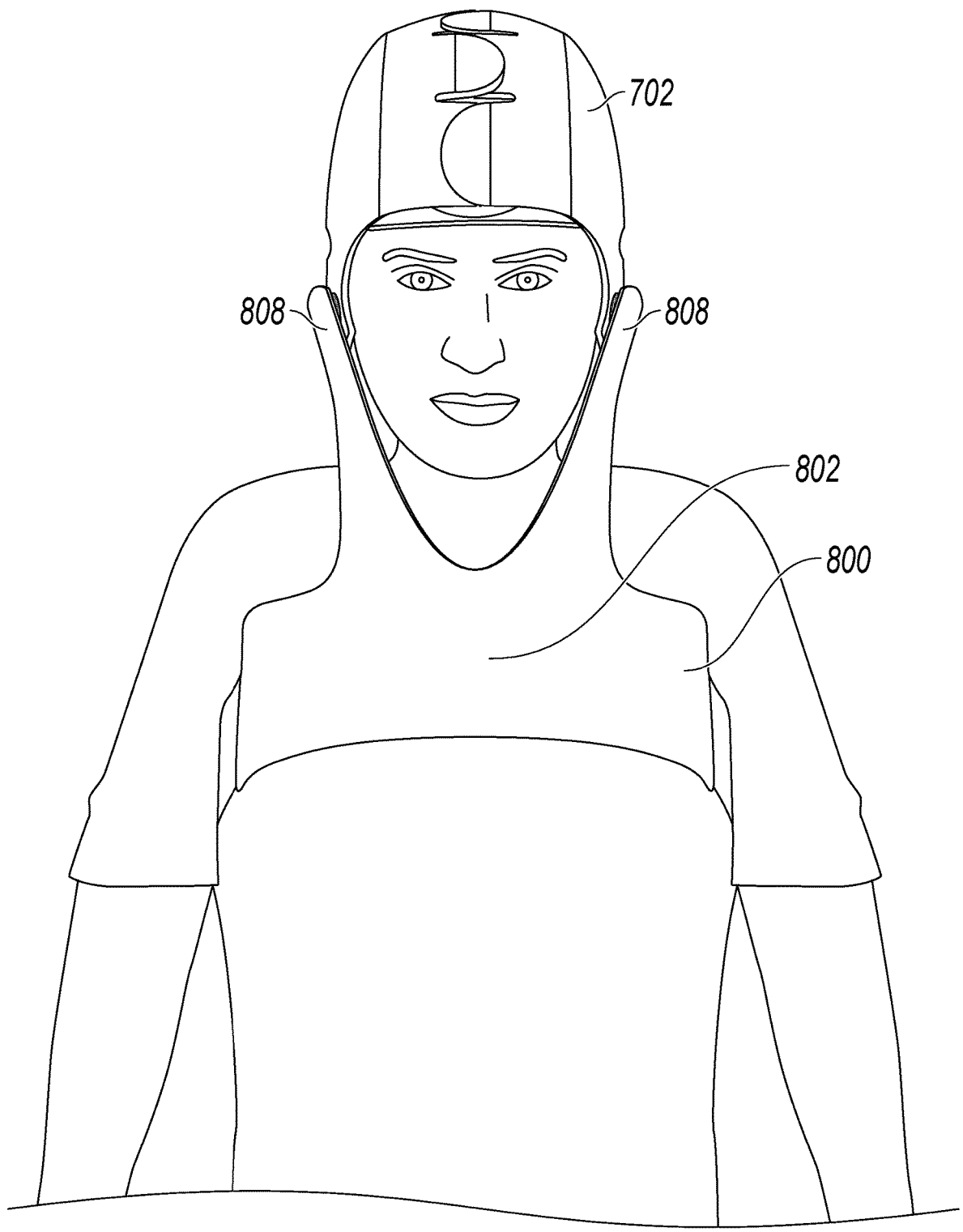
FIG. 8B is a front view showing a cap utilizing the illustrative cap securement device.
Figure 8C:
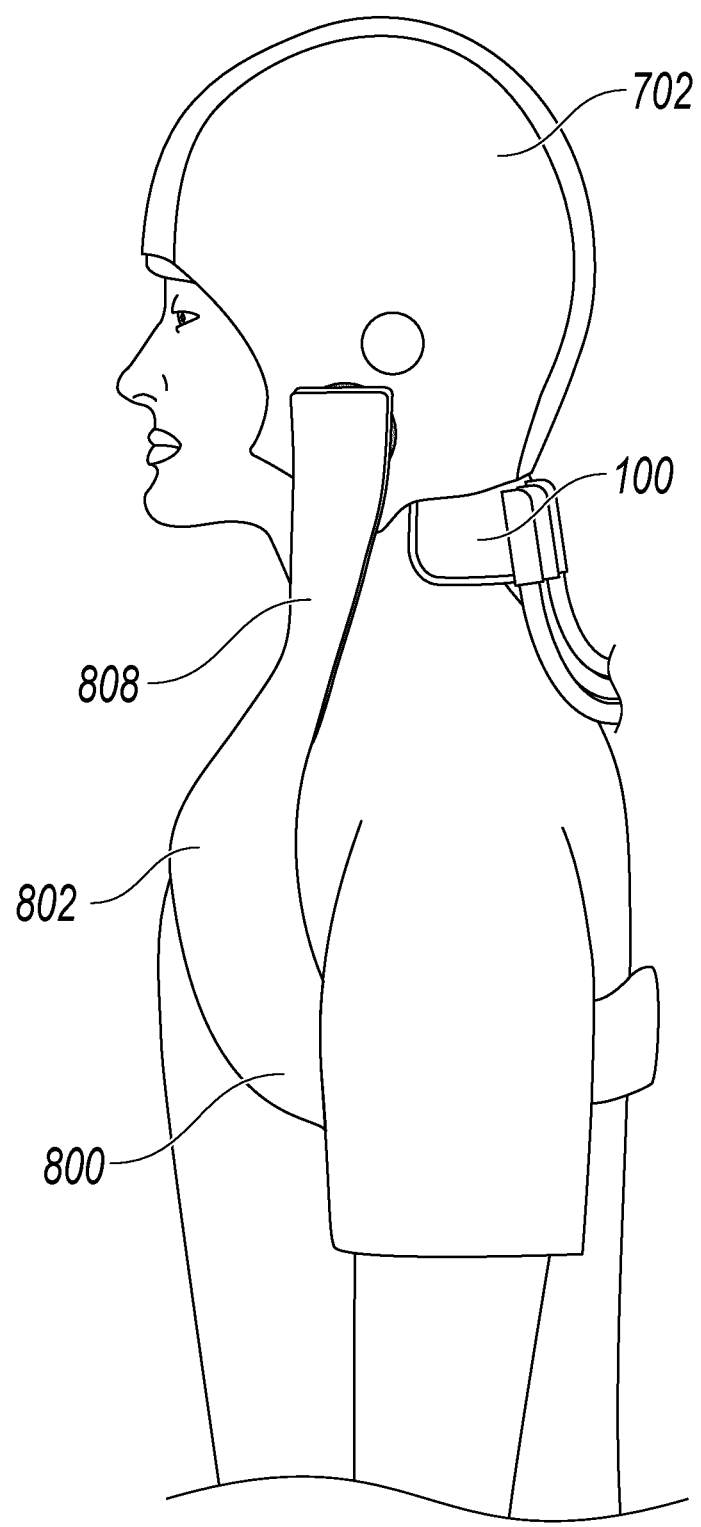
FIG. 8C is a side view showing a cap utilizing the illustrative cap securement device.

FIG. 8A is a perspective view of an embodiment of a securement device 800. FIG. 8B is a front view showing the cap 702 utilizing the cap securement device 800. FIG. 8C is a side view showing the cap 702 utilizing the cap securement device 800. The cap securement device 800 includes a torso pad 802. The cap securement device 800 is utilized in lieu of the chin portion 708 to facilitate comfort of the wearer. A stiffening element (not explicitly shown) is inserted into the torso pad 802 in an effort to prevent buckling of the torso pad 802 during use. A first strap 804 and a second strap 806 extend laterally from opposite sides of the torso pad 802. In use, the first strap 804 is adjustably coupled to the second strap 806 about an upper torso region of the wearer. The cap securement device 800 includes a pair of temporal straps 808 extending from the torso pad 802. In use, the pair of temporal straps 808 are connected to a temporal region of the cap 702. Connection of the temporal straps 808 to the cap imparts a downward force a downward force to the cap 702 and facilitates accommodation of a variety of head shapes and achieve better conformity and fitting against a head of a wearer.

Figure 9:
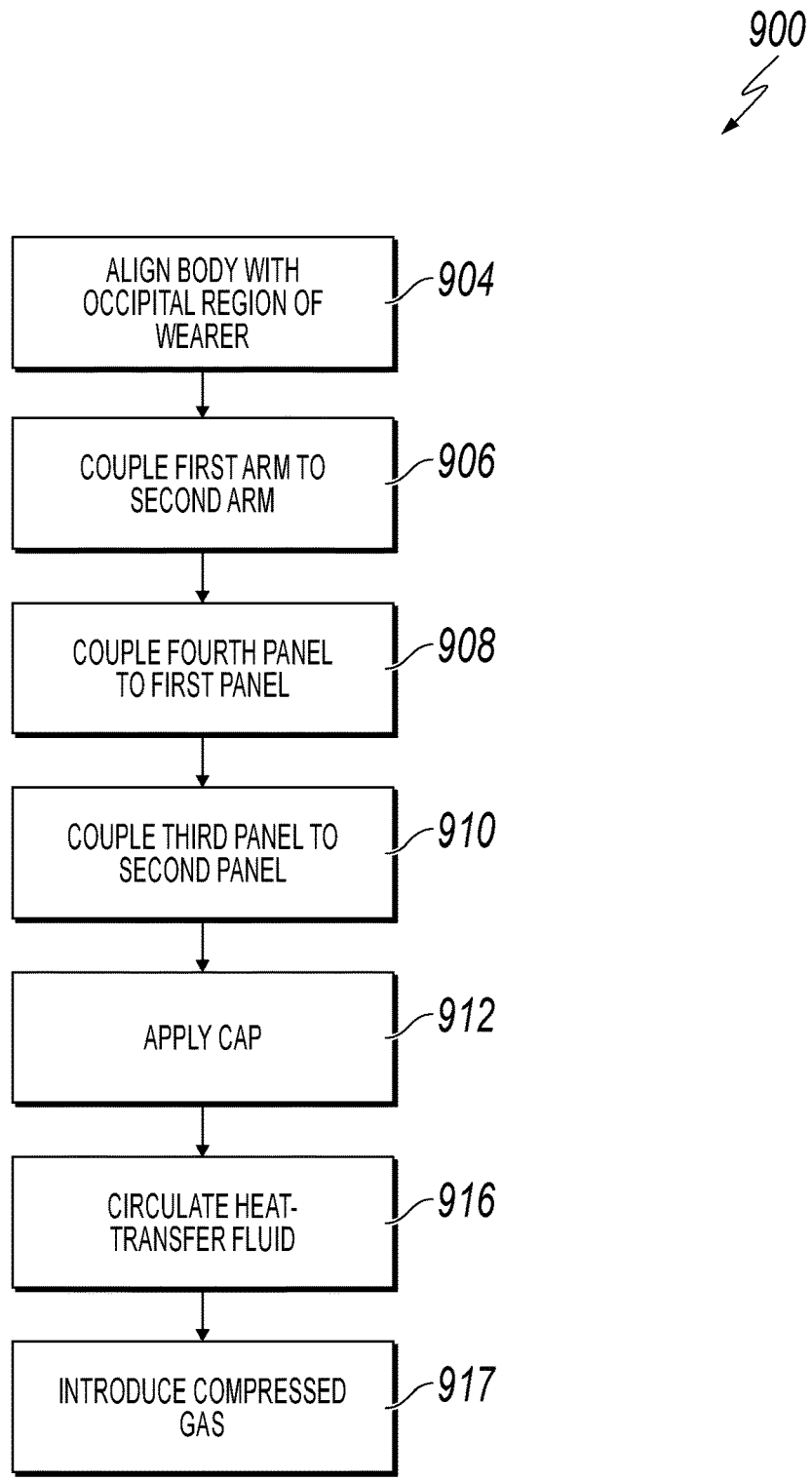
FIG. 9 is a flow diagram illustrating a process for applying the illustrative head wrap.

FIG. 9 is a flow diagram illustrating a process 900 for applying the illustrative head wrap 100 in accordance with one or more aspects of the disclosure. At block 904, an interior aspect of the body 102 is aligned with an occipital region the wearer's head. At block 906, the first arm 104 is coupled to the second arm 106 in the region of the wearer's forehead. At block 908, the fourth panel 124 is coupled to the first panel 114 and the third panel 122 is coupled to the second panel 116. At block 910, the center section 108 is folded over a top of the wearer's head and coupled to at least one of the first arm 104 and the second arm 106 in the region of the wearer's forehead. In various embodiments, blocks 904-910 may be performed in any order. At block 912, the cap 702 is applied to the wearer's head to secure the head wrap 100. At block 916, heat-transfer fluid is circulated through the fluid bladder 150. The heat-transfer fluid is introduced to the fluid bladder 150 via the first fluid port 134 and the heat-transfer fluid is removed from the fluid bladder via the second fluid port 136; however, in other embodiments the fluid flow may be reversed. The heat-transfer fluid removes heat from the wearer's scalp thereby cooling the wearer's scalp to a temperature below nominal scalp temperature. Such cooling has been shown to be effective in preventing the onset of alopecia in patients undergoing treatments such as, for example chemotherapy and radiation therapy. In other embodiments, the heat-transfer fluid can be circulated through the head wrap 100 in order to add heat to the wearer's scalp thereby warming the wearer's scalp to a temperature above nominal scalp temperature. Such treatments can be useful in the treatment of, for example, migranes and strokes. At block 917, compressed gas is introduced to the compression bladder 151 via the compression port 138. The compressed gas inflates the compression bladder 151 and imparts a downward force on the fluid bladder 150. Such downward force ensures intimate contact of the fluid bladder 150 with the wearer's scalp and prevents puckering of the fluid bladder 150. Such puckering can cause areas of the wearer's scalp to not be sufficiently thermally exposed to the fluid bladder 150 resulting in small areas of alopecia developing on the wearer's scalp.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure. The scope of the invention should be determined by the language of the claims that follow. The term "comprising" within the claims is intended to mean "including at least" such that the recited list of elements in a claim are an open group. The terms "a," "an," and other singular terms are intended to include the plural forms thereof unless specifically excluded.

What is claimed is:

1. A head wrap for conforming to a wearer's scalp, the head wrap comprising:
    a first layer formed of a flexible material and adapted to be placed in contact with the wearer's scalp, the first layer comprising a first-layer perimeter;
    a second layer adjacent to the first layer, the second layer comprising a second-layer perimeter that is bonded to the first-layer perimeter;
    a plurality of second bonds joining the first layer to the second layer, the plurality of second bonds being formed interior of the first-layer perimeter and the second-layer perimeter; and
    wherein, in use, the first layer and the second layer define a first arm and a second arm, the first arm and the second arm defining a common axis bisecting a longitudinal portion of the first arm and the second arm, and a plurality of rounded projections extending upwardly from each of the first arm and the second arm on the same side of the common axis as a center rounded projection, the first arm, the second arm, the plurality of rounded projections and the center rounded projection being selectively foldable from a generally flat configuration to overlap into a three-dimensional configuration to conform to the wearer's head such that the center rounded projection overlaps one of the first and second arms.

2. The head wrap of claim 1, comprising:
    a first fluid port fluidly coupled to a fluid bladder defined by the first layer and the second layer; and
    a second fluid port fluidly coupled to the fluid bladder.

3. The head wrap of claim 2, wherein the first fluid port and the second fluid port are formed between the first layer and the second layer.

4. The head wrap of claim 1, comprising:
    a third layer adjacent to the second layer, the third layer comprising a third-layer perimeter that aligns with and is bonded to the first layer perimeter and the second-layer perimeter;
    a compression bladder defined between the second layer and the third layer; and
    wherein, in use, the third layer is selectively foldable from a generally flat configuration into a three-dimensional configuration to conform to the wearer's head.

5. The head wrap of claim 4, comprising a compression port fluidly coupled to the compression bladder.

6. The head wrap of claim 5, wherein the compression port is disposed between the second layer and the third layer.

7. The head wrap of claim 4, comprising a first fluid port and a second fluid port that penetrate the third layer and are sealed to the second layer.

8. The head wrap of claim 4, comprising a fourth layer adjacent to the third layer, the fourth layer being bonded to the third layer to provide compression at select locations on the wearer's scalp.

9. The head wrap of claim 1, wherein the plurality of second bonds define a plurality of flow paths through a fluid bladder and limit an amount of heat-transfer fluid contained in the fluid bladder.

10. A head wrap for conforming to a wearer's head, the head wrap comprising:
    a body;
    a first arm extending longitudinally from the body along a common axis defined longitudinally through and bisecting a longitudinal portion of the first arm and a second arm;
    the second arm extending longitudinally from the body oppositely from, and sharing the common axis with, the first arm;
    a center rounded projection extending from the body generally perpendicular to the first arm and the second arm;
    a first rounded projection extending from the first arm on the same side of the common axis as the center rounded projection;
    a fourth rounded projection extending from the second arm on the same side of the common axis as the center rounded projection;
    a fluid bladder defined by the body, the first arm, the second arm, and the center rounded projection; and
    a first fluid port formed in the body and fluidly coupled to the fluid bladder and a second fluid port formed in the body and fluidly coupled to the fluid bladder;
    a second rounded projection extending from the first arm on the same side of the common axis as the center rounded projection;

a third rounded projection extending from the second arm on the same side of the common axis as the center rounded projection; and the center rounded projection overlapping one of the first and second arms, in use.

11. The head wrap of claim 10, wherein:

the first rounded projection extends at an angle relative to the common axis; and the second rounded projection is angled relative to the common axis in a direction generally opposite the first rounded projection.

12. The head wrap of claim 10, wherein:

the third rounded projection extends at an angle relative to the common axis; and the fourth rounded projection is angled relative to the common axis in a direction generally opposite the third rounded projection.

13. The head wrap of claim 10, comprising a compression bladder disposed outwardly of the fluid bladder and coextensive with the fluid bladder.

14. A method of using a head wrap to conform to a wearer's head, the method comprising:

applying a body of the head wrap to an occipital region of a wearer's scalp;

coupling a first arm that extends from the body to a second arm that extends from the body, the second arm extending along a common axis bisecting a longitudinal portion of the first arm and the second arm;

coupling a first rounded projection that extends from the first arm to a fourth rounded projection that extends from the second arm, the first rounded projection and the fourth rounded projection extending from the first arm on the same side of the common axis as a center rounded projection;

coupling a second rounded projection that extends from the first arm to a third rounded projection that extends from the second arm, the second rounded projection and the third rounded projection extending from the second arm on the same side of the common axis as the center rounded projection;

coupling the center rounded projection that extends from the body to at least one of the first arm and the second arm, the center rounded projection overlapping at least one of the first arm and the second arm; and circulating a heat-transfer fluid through a fluid bladder via a first fluid port and a second fluid port.

15. The method of claim 14, comprising applying a compressed gas to a compression bladder via a compression port.

16. The method of claim 14, comprising:

placing a cap on the wearer's head over the head wrap;

adjusting the cap via selective adjustable connection of a plurality of tabs, the plurality of tabs being aligned with a sagittal line of the wearer's scalp; and securing the cap.

17. The method of claim 16, wherein the securing the cap comprises utilizing at least one of a cap securement device and a chin portion.

18. The method of claim 14, comprising at least one of cooling and heating the scalp via application of the heat-transfer fluid.

* * * * *